US006172193B1

(12) United States Patent
Primi et al.

(10) Patent No.: US 6,172,193 B1
(45) Date of Patent: Jan. 9, 2001

(54) ESCAPE MUTANT OF THE SURFACE ANTIGEN OF HEPATITIS B VIRUS

(75) Inventors: Daniele Primi, Brescia; Gianfranco Fiordalisi, Breno Brescia; Mario Palla, Saluggia, all of (IT)

(73) Assignee: DiaSorin International Inc., New York, NY (US)

( * ) Notice: Under 35 U.S.C. 154(b), the term of this patent shall be extended for 0 days.

(21) Appl. No.: 09/193,104

(22) Filed: Nov. 16, 1998

(30) Foreign Application Priority Data

Dec. 1, 1997 (EP) ........................................ 97830635

(51) Int. Cl.[7] .............................................. A61K 39/29
(52) U.S. Cl. ....................................... 530/350; 530/826
(58) Field of Search .................................. 530/350, 826

(56) References Cited

U.S. PATENT DOCUMENTS

| | | |
|---|---|---|
| 5,286,452 | 2/1994 | Hansen . |
| 5,589,401 | 12/1996 | Hansen et al. . |
| 5,639,637 | 6/1997 | Thomas et al. . |

FOREIGN PATENT DOCUMENTS

| | | |
|---|---|---|
| 0 511 855 A1 | 11/1992 | (EP) . |
| 0 522 030 B1 | 1/1993 | (EP) . |
| WO 87/06594 | 11/1987 | (WO) . |
| WO 94/21812 | 9/1994 | (WO) . |
| WO 94/25486 | 11/1994 | (WO) . |
| WO 94/26904 | 11/1994 | (WO) . |
| WO 95/21189 | 8/1995 | (WO) . |
| WO 97/39029 | 10/1997 | (WO) . |
| WO 98/45421 | 10/1998 | (WO) . |

OTHER PUBLICATIONS

European Search Report for Application No. 97830635.5, dated Apr. 8, 1999.

Antoni et al., "Site–directed Mutagenesis of Cysteine Residues of Hepatitis B Surface Antigen," *Eur. J. Biochem.*, 222(1):121–127 (May 1994).

Ashton–Rickardt et al., "Mutants of the Hepatitis B Virus Surface Antigen that Define Some Antigenically Essential Residues in the Immunodominant a Region," *J. Med. Virol.*, 29(3):196–203 (Nov. 1989). (abstract only).

Ashton–Rickardt et al., "Mutations that Change the Immunological Subtype of Hepatitis B Virus Surface Antigen and Distinguish Between Antigenic and Immunogenic Determination," *J. Med. Virol.*, 29(3):204–214 (Nov. 1989). (abstract only).

Bruce et al., "Mutations of Some Critical Amino Acid Residues in the Hepatitis B Virus Surface Antigen," *J. Med. Virol.*, 46(2):157–161 (Jun. 1995).

Cariani et al., "Emergence of Hepatitis B Virus S Geene Mutant in a Liver Transplant Recipient," *J. Med. Virol.*, 47:410–415 (1995).

Carman et al., "Vaccine–induced Escape Mutant of Hepatitis B Virus," *The Lancet*, 336:325–329 (Aug. 11, 1990).

Grethe et al., "Characterization of Unusual Escape Variants of Hepatitis B Virus Isolated From a Hepatitis B Surface Antigen–Negative Subject," *J. Virol.*, 72(9):7692–7696 (Sep. 1998).

Howard et al., "Hepatitis B Surface Antigen Variation and Protective Immunity," *Intervirology*, 38:35–40 (1995).

Mangold et al., "Secretion and Antigenicity of Hepatitits B Virus Small Envelope Proteins Lacking Cysteines in the Major Antigenic Region," *Virology*, 211(2):535–543 (Aug. 20, 1995).

McMahon et al., "Genetic Alterations in the Gene Encoding the Major HBsAg: DNA and Immunological Analysis of Recurrent HBsAg Derived from Monoclonal Antibody–treated Liver Transplant Patients," *Hepatology*, 15(5):757–766 (1992).

Moriyama et al., "Immunoselected Hepatitis B Virus Mutant," *The Lancet*, 337:125 (Jan. 12, 1991).

Ni et al., "A New Immune Escape Mutant of Hepatitis B Virus with an Asp to Ala Substitution in aa144 of the Envelope Major Protein," *Res. Virol.*, 146(6):397–407 (Nov.–Dec. 1995). (abstract only).

Okamoto et al., "The Loss of Subtypic Determinants in Alleles, d/y or w/r, on Hepatitis B Surface Antigen," *Mol. Immunol.*, 26(2);197–205 (Feb. 1989). (abstract only).

Okamoto et al., "Mutations within the S Gene of Hepatitis B Virus Transmitted From Mothers to Babies Immunized with Hepatitis B Immune Globulin and Vaccine," *Pediatr. Res.*, 32(3):264–268 (Sep. 1992). (abstract only).

Ren et al., "Expression of 12 Antibody Escape Mutants of Hepatitis B Virus Surface Antigen Gene in Mammalian Cell by Using an Epstein–Barr Based Vector," *Chung Hua I Hsueh Tsa Chih*, 75(7):396–398, 444–445 (Jul. 1995). (abstract only).

Shiau et al., "Mutated Epitopes of Hepatitis B Surface Antigen Fused to the Core Antigen of the Virus Induce Antibodies that React with the Native Surface Antigen," *J. Med. Virol.*, 51(3):159–166 9Mar. 1997).

Sorin Biomedica, "Kit for Qualitative Immunoenzymic Determination of Hepatitis B Surface Antigen (HBsAg) in Serum or Plasma Samples, ETI–MAK–3," Sep. 1993.

(List continued on next page.)

*Primary Examiner*—Donna C. Wortman
*Assistant Examiner*—Brenda G. Brumback
(74) *Attorney, Agent, or Firm*—Popovich & Wiles, P.A.

(57) ABSTRACT

The invention provides an isolated mutant hepatitis B surface antigen protein which comprises an amino acid sequence of a surface antigen protein of hepatitis B virus which infects humans, in which the amino acid at position 121 is not cysteine and. at least one of the amino acids at positions 120, 122, 123, 147, or 149 is not a conserved amino acid for its position. The invention also provides a method for detecting in a sample a mutant hepatitis B surface antigen protein or a particle containing the protein.

34 Claims, 12 Drawing Sheets

OTHER PUBLICATIONS

Valenzuela et al., "Nucleotide Sequence of the Gene Coding for the Major Protein of Hepatitis B Virus Surface Antigen," *Nature*, 280(5725):815–819 (Aug. 1979).

Wang et al., "Sequencing of Hepatitis B Virus DNA Fragment Coding Major HBsAg of Escape Mutant," *Chung Hua I Hsueh Tsa Chig*, 74(6):355–357, 391 (Jun. 1994). (abstract only).

Yamamoto et al., "Naturally Occurring Escape Mutants of Hepatitis B Virus with Various Mutations in the S Gene in Carriers Seropositive for Antibody to Hepatitis B surface Antigen," *J. Virol.*, 68(4):2671–2676 (Apr. 1994).

Zuckerman et al., "Mutations in S Region of Hepatitis B Virus," *The Lancet*, 343:737–738 (Mar. 19, 1994).

CLRRFIIFLFILLLCLIFLLALLDYQGMLPVCPLIPGLSTIRTGAYQPCTTIAQ
GTSTYPSCCCIKPSDGNYTYIPIPSSWAFGKFLWEWAS (SEQ ID NO:2)

Fig. 1

HBVAYW3
CLRRFIIFLFILLLCLIFLLVLLDYQGMLPVCPLIPGSSTTSTGPCRTCM 50
HBVADR
CLRRFIIFLFILLLCLIFLLVLLDYQGMLPVCPLIPGTSTTSTGPCKTCT 50
HBVADW 2
CLRRFIIFLFILLLCLIFLLVLLDYQGMLPVCPLIPGSSTTSTGPCKTCT 50
HBVAYW
CLRRFIIFLFILLLCLIFLLVLLDYQGMLPVCPLIPGSSTTSTGPCRTCT 50
CTS
CLRRFIIFLFILLLCLIFLLALLDYQGMLPVCPLIPGLSTIRTGAYQPCT 50

HBVAYW3
TTAQGTSMYPSCCCTKPSDGNCTCIPIPSSWAFGKFLWEWAS 92
(SEQ ID NO:3)
HBVADR
IPAQGTSMFPSCCCTKPSDGNCTCIPIPSSWAFARFLWEWAS 92
(SEQ ID NO:4)
HBVADW2
TPAQGNSMFPSCCCSKPTDGNCTCIPIPSSWAFGKYLWEWAS 92
(SEQ ID NO:5)
HBVAYW
TPAQGTSMYPSCCCTKPSDGNCTCIPIPSSWAFGKFLWEWAS 92
(SEQ ID NO:6)
CTS
TIAQGTSTYPSCCCIKPSDGNYTYIPIPSSWAFGKFLWEWAS 92
(SEQ ID NO:2)

Fig. 2

7AYWS
SWWTSLNFRGGTTVCLGQNSQSPTSNHSPTSCPPTCPGYRWMCLRGFIIF 50
6AYWS
SWWTSLNFLGGTTVCLGQNSQSPTSNHSPTSCPPICPGYRWMCLRRFIIF 50
3AYWS
SWWTSLNFLGGTTVCLGQNSQSPTSNHSPTSCPPTCPGYRWMCLRRFIIF 50
2AYWS
SWWTSLNFLGGTTVCLGQNSQSPTSNHSPTSCPPTCPGYRWMCLRRFIIF 50
1AYWS
SWWTSLNFLGGTTVCLGQNSQSPTSNHSPTSCPPTCPGYRWMCLRRFIIF 50
1ADYWS
SWWTSLNFLGGTTVCLGQNSQSPISNHSPTSCPPTCPGYRWMCLRRFIIF 50
5AYWS
SWWTSLNFLGGTTVCLGQNSQSPTSNHSPTSCPPTCPGYRWMSRRRFIIF 50
5ADWS
SWWTSLNFLGGTPVCLGQNSQSQISSHSPTCCPPICPGYRWMCLRRFIIF 50
2ADWS
SWWTSLNFLGGTPVCLGQNSQSQISSHSPTCCPPICPGYRWMCLRRFIIF 50
3ADWMUT
SWWTSLSFLGGTPVCLGQNSQSQISSHSPTCCPPICPGYRWMCLRRFIIF 50
2ADWMUT
SWWTSLNFLGGTPVCLGQNSQSQISSHSPTCCPPICPGYRWMCLRRFIIF 50
1ADWS
SWWTSLNFLGGTPVCLGQNSQSQISSHSPTCCPPICPGYRWMCLRRFIIF 50
4ADWMUT
SWWTSLNFIGGSPVCLGQNSQSPTSNHSPTSCPPICPGYRWMCLRRFIIF 50
3ADWS
SWWTSLNFLGGSPVCLGQNSRSPTSNHSPTSCPPICPGYRWMCLRRFIIF 50
1ADWMUT
SWWTSLNFLGGSPVCLGQNSQSPTSNHSPTSCPPICPGYRWMCLRRFIIF 50
4ADRS
SWWTSLNFLGGAPTCPGQNSQSPTSNHSPTSCPPICPGYRWMCLRRFIIF 50
1ADRS
SWWTSLNFLGGAPTCPGQNSQSPTSNHSPTSCPPTCPGYRWMCLRRFIIF 50

Fig. 3A

```
3ADRS
SWWTSLNFLGEAPTCPGQNSQSPTSNHSPTSCPPICPGYRWMCLRRFIIF  50
2ADRS
SWWTSLNFLGGAPTCPGRNSQSPTSNHSPTSCPPICPGYRWMCLRRFIIF  50
4ADWS
SWWTSLNFLGGLPGCPGQNSQSPTSNHLPTSCPPTCPGYRWMCLRRFIIF  50
CTS
SWWTSLNFLGGTTVCLGQNSQSPTSNHSPTSCPPTCPGYRWMCLRRFIIF  50
******.* *. . * *.**.*..*.* **.***.*******. * ****


7AYWS
LFILLLCLIFLLVLLEYQGMLHVCPLIPGTTTTSTGPCKTCTTPAQGNSM 100
6AYWS
LFILLLCLIFLLVLLDYQGMLPVCPLIPGSSTTSTGPCRTCTTPAQGTSM 100
3AYWS
LFILLLCLIFLLVLLDYQGMLPVCPLIPGSSTTSTGPCRTCTTPAQGTSM 100
2AYWS
LFILLLCLIFLLVLLDYQGMLPVCPLIPGSSTTSTGPCRTCTTPAQGNSM 100
1AYWS
LFILLLCLIFLLVLLDYQGMLPVCPLIPGSSTTSTGPCRTCMTTAQGTSM 100
1ADYWS
LFILLLCLIFLLVLLDYQGMLPVCPLIPGSSTTSTGSCRTCTTPAQGISM 100
5AYWS
LFILLLCLIFLLVLLDYQGMLPVCPLIPGSSTTSTGPCRTCTTPAQGTSM 100
5ADWS
LCILLLCLIFLLVLLDYQGMLPVCPLILGSSTTSTGPCKTCTTPAQGTSM 100
2ADWS
LCILLLCLIFLLVLLDYQGMLPVCPLIPGSSTTSTGPCKTCTTPAQGTSM 100
3ADWMUT
LCILLLCLIFLLVLLDYQGMLPVCPLIPGSSTTSTGPCKTCTTPAQGTSM 100
2ADWMUT
LCILLLCLIFLLVLLDYQGMLPVCPLIPGSSTTSTGPCKICTTPAQGTSM 100
```

Fig. 3B

1ADWS
LCILLLCLIFLLVLLDYQGMLPVCPLIPGSSTTSTGPCKTCTTPAQGTSM 100
4ADWMUT
LFILLLCLIFLLVLLDYQGMLPVCPLIPGSTTTSTGPCKTCTTPAQGNSM 100
3ADWS
LFILLLCLIFLLVLLDYQGMLPVCPLILGSTTTSTGPCKTCTTPAQGNSM 100
1ADWMUT
LFILLLCLIFLLVLLDYQGMLPVCPIIPGSTTTSTGPCKTCTTPAQGNSL 100
4ADRS
LFILLLCLIFLLVLLDYQGMLPVCPLLPGTSTTSTGPCKTCTIPAQGTSM 100
1ADRS
LFILLLCLIFLLVLLDYQGMLPVCPLLPGTSTTSTGPCKTCTIPAQGTSM 100
3ADRS
LFILLLCLIFLLVLLDYQGMLPVCPLLPGTSTTSTGPCKTCTIPAQGTSM 100
2ADRS
LFILLLCLIFLLVLLDYQGMLPVCPLLPGTSTTSTGPCKTCTTPAQGNSM 100
4ADWS
LFILLLCLIFLLVLLDYQGMLPVCPLLPGSTTTSTGPCKTCTTLAQGTSM 100
CTS
LFILLLCLIFLLALLDYQGMLPVCPLIPGLSTIRTGAYQPCTTIAQGTST 100
* ********..***.*.. * .*..**... * . *** *

7AYWS
FPSCCCTKTSDGNCTCIPIPSSWAFAKYLWEWASVRFSWLSLLVPFVQWF 150
6AYWS
YPSCCCTKPSHGNCTCIPIPSSWAFGKFLWEWASARFSWLSLLVPFVQWF 150
3AYWS
YPSCCCTKPSDGNCTCIPIPSSWAFGKFLWEWASARFSWLSLLVPFVQWF 150
2AYWS
YPSCCCTKPSDGNCTCIPIPSSWAFGKFLWEWASARFSWLSLLVPFVQWF 150
1AYWS
YPSCCCTKPSDGNCTCIPIPSSWAFGKFLWEWASARFSWLSLLVPFVQWF 150
1ADYWS
YPSCCCTKPSDGNCTCIPIPSSWAFGKFLWEWASARFSWLSLLVPFVQWF 150

Fig. 3C

5AYWS
YPSCCCTKPSDGNCTCIPIPSSWAFGKFLWEWASARFSWLSLLVGFVQWF 150
5ADWS
FPSCCCTKPTDGNCTCIPIPSSWAFAKYLWEWASVRFSWLSLLVPFVQWF 150
2ADWS
FPSCCCTKPTDGNCTCIPIPSSWAFAKYLWEWASVRFSWLSLLVPFVQWF 150
3ADWMUT
FPSCCCTKPTDGNCTCIPIPSSWAFAKYLWEWASVRFSWLSLLVPFVQWF 150
2ADWMUT
FPSCCCTKPTDGNCTCIPIPSSWAFAKYLWEWASVRFSWLSLLVPFVQWF 150
1ADWS
FPSCCCTKPMDGNCTCIPIPSSWAFAKYLWEWASVRFSWLSLLVPFVQWF 150
4ADWMUT
FPSCCCTKPTVGNCTCIPIPSSWAFAKYLWEWASVRFSWLSLLVPFVQWF 150
3ADWS
FPSCCCTKPTDGNCTCIPIPSSWAFAKYLWEWASVRFSWLSLLVPFVQWF 150
1ADWMUT
FPSCCCTKPTDGNCTCIPIPSSWAFAKYLWERASVRFSWLSLLVPFVQWF 150
4ADRS
FPSCCCTKPSDGNCTCIPIPSSWAFARFLWEGASVRFSWLSLLVPFVQWF 150
1ADRS
FPSCCCTKPSDGNCTCIPIPSSWAFARFLWEWASVRFSWLSLLVPFVQWF 150
3ADRS
FPSCCCTKPSDGNCTCIPIPSSWAFARFLWEWASVRFSWLSLLVPFVQWF 150
2ADRS
FPSCCCTKPSDGNCTCIPIPSSWAFARFLWEWASVRFSWLSLLVPFVQWF 150
4ADWS
FPSCCCSKPSDGNCTCIPIPSSWALGKYLWEWASARFSWLSLLVQFVQWC 150
CTS
YPSCCCIKPSDGNYTYIPIPSSWAFGKFLWEWASARFSWLSLLVPFVQWF 150
.***** *.  ***********....* .***** **

Fig. 3D

| | | | |
|---|---|---|---|
| 7AYWS | VGLS | 154 | (SEQ ID NO:7) |
| 6AYWS | MGLS | 154 | (SEQ ID NO:8) |
| 3AYWS | VGLS | 154 | (SEQ ID NO:9) |
| 2AYWS | VGLS | 154 | (SEQ ID NO:10) |
| 1AYWS | VGLS | 154 | (SEQ ID NO:11) |
| 1ADYWS | VGLS | 154 | (SEQ ID NO:12) |
| 5AYWS | VGLS | 154 | (SEQ ID NO:13) |
| 5ADWS | VGLS | 154 | (SEQ ID NO:14) |
| 2ADWS | VGLS | 154 | (SEQ ID NO:15) |
| 3ADWMUT | VGLS | 154 | (SEQ ID NO:16) |
| 2ADWMUT | VGLS | 154 | (SEQ ID NO:17) |
| 1ADWS | VGLS | 154 | (SEQ ID NO:18) |
| 4ADWMUT | VGLS | 154 | (SEQ ID NO:19) |
| 3ADWS | VGLS | 154 | (SEQ ID NO:20) |
| 1ADWMUT | VGLS | 154 | (SEQ ID NO:21) |
| 4ADRS | VGLS | 154 | (SEQ ID NO:22) |
| 1ADRS | VGLS | 154 | (SEQ ID NO:23) |
| 3ADRS | AGLS | 154 | (SEQ ID NO:24) |
| 2ADRS | VGLS | 154 | (SEQ ID NO:25) |
| 4ADWS | VGLS | 154 | (SEQ ID NO:26) |
| CTS | AGLS | 154 | (SEQ ID NO:27) |
| | *** | | |

Fig. 3E

SEQUENCE LISTING

```
<160> NUMBER OF SEQ ID NOS: 44

<210> SEQ ID NO 1
<211> LENGTH: 276
<212> TYPE: DNA
<213> ORGANISM: Hepatitis B virus
<220> FEATURE:
<221> NAME/KEY: CDS
<222> LOCATION: (1)..(276)

<400> SEQUENCE: 1

tgt ctg cgg cgt ttt atc atc ttc ctc ttc atc ctg ctg cta tgc ctc       48
Cys Leu Arg Arg Phe Ile Ile Phe Leu Phe Ile Leu Leu Leu Cys Leu
  1               5                  10                  15

atc ttc ttg ttg gct ctt ctg gac tat caa ggt atg ttg ccc gtt tgt       96
Ile Phe Leu Leu Ala Leu Leu Asp Tyr Gln Gly Met Leu Pro Val Cys
             20                  25                  30

cct cta att cca gga ctc tcg acc atc cgc acg gga gca tac caa ccc      144
Pro Leu Ile Pro Gly Leu Ser Thr Ile Arg Thr Gly Ala Tyr Gln Pro
         35                  40                  45

tgc acg act att gct caa gga acc tct acg tat ccc tcc tgt tgc tgt      192
Cys Thr Thr Ile Ala Gln Gly Thr Ser Thr Tyr Pro Ser Cys Cys Cys
     50                  55                  60

atc aaa cct tcg gac gga aat tac acc tat att ccc atc cca tca tcc      240
Ile Lys Pro Ser Asp Gly Asn Tyr Thr Tyr Ile Pro Ile Pro Ser Ser
 65                  70                  75                  80

tgg gct ttc gga aaa ttc cta tgg gag tgg gcc tca                      276
Trp Ala Phe Gly Lys Phe Leu Trp Glu Trp Ala Ser
                 85                  90


<210> SEQ ID NO 2
<211> LENGTH: 92
<212> TYPE: PRT
<213> ORGANISM: Hepatitis B virus

<400> SEQUENCE: 2

Cys Leu Arg Arg Phe Ile Ile Phe Leu Phe Ile Leu Leu Leu Cys Leu
  1               5                  10                  15

Ile Phe Leu Leu Ala Leu Leu Asp Tyr Gln Gly Met Leu Pro Val Cys
             20                  25                  30

Pro Leu Ile Pro Gly Leu Ser Thr Ile Arg Thr Gly Ala Tyr Gln Pro
         35                  40                  45

Cys Thr Thr Ile Ala Gln Gly Thr Ser Thr Tyr Pro Ser Cys Cys Cys
     50                  55                  60

Ile Lys Pro Ser Asp Gly Asn Tyr Thr Tyr Ile Pro Ile Pro Ser Ser
 65                  70                  75                  80

Trp Ala Phe Gly Lys Phe Leu Trp Glu Trp Ala Ser
                 85                  90


<210> SEQ ID NO 3
<211> LENGTH: 92
<212> TYPE: PRT
<213> ORGANISM: Hepatitis B virus

<400> SEQUENCE: 3

Cys Leu Arg Arg Phe Ile Ile Phe Leu Phe Ile Leu Leu Leu Cys Leu
  1               5                  10                  15

Ile Phe Leu Leu Val Leu Leu Asp Tyr Gln Gly Met Leu Pro Val Cys
             20                  25                  30
```

-continued

```
Pro Leu Ile Pro Gly Ser Ser Thr Thr Ser Thr Gly Pro Cys Arg Thr
        35                  40                  45

Cys Met Thr Thr Ala Gln Gly Thr Ser Met Tyr Pro Ser Cys Cys Cys
    50                  55                  60

Thr Lys Pro Ser Asp Gly Asn Cys Thr Cys Ile Pro Ile Pro Ser Ser
 65                 70                  75                  80

Trp Ala Phe Gly Lys Phe Leu Trp Glu Trp Ala Ser
                85                  90


<210> SEQ ID NO 4
<211> LENGTH: 92
<212> TYPE: PRT
<213> ORGANISM: Hepatitis B virus

<400> SEQUENCE: 4

Cys Leu Arg Arg Phe Ile Ile Phe Leu Phe Ile Leu Leu Leu Cys Leu
  1               5                  10                  15

Ile Phe Leu Leu Val Leu Leu Asp Tyr Gln Gly Met Leu Pro Val Cys
             20                  25                  30

Pro Leu Ile Pro Gly Thr Ser Thr Thr Ser Thr Gly Pro Cys Lys Thr
        35                  40                  45

Cys Thr Ile Pro Ala Gln Gly Thr Ser Met Phe Pro Ser Cys Cys Cys
    50                  55                  60

Thr Lys Pro Ser Asp Gly Asn Cys Thr Cys Ile Pro Ile Pro Ser Ser
 65                 70                  75                  80

Trp Ala Phe Ala Arg Phe Leu Trp Glu Trp Ala Ser
                85                  90


<210> SEQ ID NO 5
<211> LENGTH: 92
<212> TYPE: PRT
<213> ORGANISM: Hepatitis B virus

<400> SEQUENCE: 5

Cys Leu Arg Arg Phe Ile Ile Phe Leu Phe Ile Leu Leu Leu Cys Leu
  1               5                  10                  15

Ile Phe Leu Leu Val Leu Leu Asp Tyr Gln Gly Met Leu Pro Val Cys
             20                  25                  30

Pro Leu Ile Pro Gly Ser Ser Thr Thr Ser Thr Gly Pro Cys Lys Thr
        35                  40                  45

Cys Thr Thr Pro Ala Gln Gly Asn Ser Met Phe Pro Ser Cys Cys Cys
    50                  55                  60

Ser Lys Pro Thr Asp Gly Asn Cys Thr Cys Ile Pro Ile Pro Ser Ser
 65                 70                  75                  80

Trp Ala Phe Gly Lys Tyr Leu Trp Glu Trp Ala Ser
                85                  90


<210> SEQ ID NO 6
<211> LENGTH: 92
<212> TYPE: PRT
<213> ORGANISM: Hepatitis B virus

<400> SEQUENCE: 6

Cys Leu Arg Arg Phe Ile Ile Phe Leu Phe Ile Leu Leu Leu Cys Leu
  1               5                  10                  15

Ile Phe Leu Leu Val Leu Leu Asp Tyr Gln Gly Met Leu Pro Val Cys
             20                  25                  30
```

-continued

```
Pro Leu Ile Pro Gly Ser Ser Thr Thr Ser Thr Gly Pro Cys Arg Thr
        35                  40                  45

Cys Thr Thr Pro Ala Gln Gly Thr Ser Met Tyr Pro Ser Cys Cys Cys
    50                  55                  60

Thr Lys Pro Ser Asp Gly Asn Cys Thr Cys Ile Pro Ile Pro Ser Ser
65                  70                  75                  80

Trp Ala Phe Gly Lys Phe Leu Trp Glu Trp Ala Ser
                85                  90


<210> SEQ ID NO 7
<211> LENGTH: 154
<212> TYPE: PRT
<213> ORGANISM: Hepatitis B virus

<400> SEQUENCE: 7

Ser Trp Trp Thr Ser Leu Asn Phe Arg Gly Gly Thr Thr Val Cys Leu
  1               5                  10                  15

Gly Gln Asn Ser Gln Ser Pro Thr Ser Asn His Ser Pro Thr Ser Cys
            20                  25                  30

Pro Pro Thr Cys Pro Gly Tyr Arg Trp Met Cys Leu Arg Gly Phe Ile
        35                  40                  45

Ile Phe Leu Phe Ile Leu Leu Leu Cys Leu Ile Phe Leu Leu Val Leu
    50                  55                  60

Leu Glu Tyr Gln Gly Met Leu His Val Cys Pro Leu Ile Pro Gly Thr
65                  70                  75                  80

Thr Thr Thr Ser Thr Gly Pro Cys Lys Thr Cys Thr Thr Pro Ala Gln
                85                  90                  95

Gly Asn Ser Met Phe Pro Ser Cys Cys Cys Thr Lys Thr Ser Asp Gly
            100                 105                 110

Asn Cys Thr Cys Ile Pro Ile Pro Ser Ser Trp Ala Phe Ala Lys Tyr
        115                 120                 125

Leu Trp Glu Trp Ala Ser Val Arg Phe Ser Trp Leu Ser Leu Leu Val
    130                 135                 140

Pro Phe Val Gln Trp Phe Val Gly Leu Ser
145                 150


<210> SEQ ID NO 8
<211> LENGTH: 154
<212> TYPE: PRT
<213> ORGANISM: Hepatitis B virus

<400> SEQUENCE: 8

Ser Trp Trp Thr Ser Leu Asn Phe Leu Gly Gly Thr Thr Val Cys Leu
  1               5                  10                  15

Gly Gln Asn Ser Gln Ser Pro Thr Ser Asn His Ser Pro Thr Ser Cys
            20                  25                  30

Pro Pro Ile Cys Pro Gly Tyr Arg Trp Met Cys Leu Arg Arg Phe Ile
        35                  40                  45

Ile Phe Leu Phe Ile Leu Leu Leu Cys Leu Ile Phe Leu Leu Val Leu
    50                  55                  60

Leu Asp Tyr Gln Gly Met Leu Pro Val Cys Pro Leu Ile Pro Gly Ser
65                  70                  75                  80

Ser Thr Thr Ser Thr Gly Pro Cys Arg Thr Cys Thr Thr Pro Ala Gln
                85                  90                  95

Gly Thr Ser Met Tyr Pro Ser Cys Cys Cys Thr Lys Pro Ser His Gly
            100                 105                 110
```

-continued

```
Asn Cys Thr Cys Ile Pro Ile Pro Ser Ser Trp Ala Phe Gly Lys Phe
        115                 120                 125

Leu Trp Glu Trp Ala Ser Ala Arg Phe Ser Trp Leu Ser Leu Leu Val
    130                 135                 140

Pro Phe Val Gln Trp Phe Met Gly Leu Ser
145                 150


<210> SEQ ID NO 9
<211> LENGTH: 154
<212> TYPE: PRT
<213> ORGANISM: Hepatitis B virus

<400> SEQUENCE: 9

Ser Trp Trp Thr Ser Leu Asn Phe Leu Gly Gly Thr Thr Val Cys Leu
  1               5                  10                  15

Gly Gln Asn Ser Gln Ser Pro Thr Ser Asn His Ser Pro Thr Ser Cys
             20                  25                  30

Pro Pro Thr Cys Pro Gly Tyr Arg Trp Met Cys Leu Arg Arg Phe Ile
        35                  40                  45

Ile Phe Leu Phe Ile Leu Leu Leu Cys Leu Ile Phe Leu Leu Val Leu
     50                  55                  60

Leu Asp Tyr Gln Gly Met Leu Pro Val Cys Pro Leu Ile Pro Gly Ser
 65                  70                  75                  80

Ser Thr Thr Ser Thr Gly Pro Cys Arg Thr Cys Thr Thr Pro Ala Gln
                 85                  90                  95

Gly Thr Ser Met Tyr Pro Ser Cys Cys Cys Thr Lys Pro Ser Asp Gly
            100                 105                 110

Asn Cys Thr Cys Ile Pro Ile Pro Ser Ser Trp Ala Phe Gly Lys Phe
        115                 120                 125

Leu Trp Glu Trp Ala Ser Ala Arg Phe Ser Trp Leu Ser Leu Leu Val
    130                 135                 140

Pro Phe Val Gln Trp Phe Val Gly Leu Ser
145                 150


<210> SEQ ID NO 10
<211> LENGTH: 154
<212> TYPE: PRT
<213> ORGANISM: Hepatitis B virus

<400> SEQUENCE: 10

Ser Trp Trp Thr Ser Leu Asn Phe Leu Gly Gly Thr Thr Val Cys Leu
  1               5                  10                  15

Gly Gln Asn Ser Gln Ser Pro Thr Ser Asn His Ser Pro Thr Ser Cys
             20                  25                  30

Pro Pro Thr Cys Pro Gly Tyr Arg Trp Met Cys Leu Arg Arg Phe Ile
        35                  40                  45

Ile Phe Leu Phe Ile Leu Leu Leu Cys Leu Ile Phe Leu Leu Val Leu
     50                  55                  60

Leu Asp Tyr Gln Gly Met Leu Pro Val Cys Pro Leu Ile Pro Gly Ser
 65                  70                  75                  80

Ser Thr Thr Ser Thr Gly Pro Cys Arg Thr Cys Thr Thr Pro Ala Gln
                 85                  90                  95

Gly Asn Ser Met Tyr Pro Ser Cys Cys Cys Thr Lys Pro Ser Asp Gly
            100                 105                 110

Asn Cys Thr Cys Ile Pro Ile Pro Ser Ser Trp Ala Phe Gly Lys Phe
        115                 120                 125
```

-continued

```
Leu Trp Glu Trp Ala Ser Ala Arg Phe Ser Trp Leu Ser Leu Leu Val
    130                 135                 140

Pro Phe Val Gln Trp Phe Val Gly Leu Ser
145                 150


<210> SEQ ID NO 11
<211> LENGTH: 154
<212> TYPE: PRT
<213> ORGANISM: Hepatitis B virus

<400> SEQUENCE: 11

Ser Trp Trp Thr Ser Leu Asn Phe Leu Gly Gly Thr Thr Val Cys Leu
  1               5                  10                  15

Gly Gln Asn Ser Gln Ser Pro Thr Ser Asn His Ser Pro Thr Ser Cys
             20                  25                  30

Pro Pro Thr Cys Pro Gly Tyr Arg Trp Met Cys Leu Arg Arg Phe Ile
         35                  40                  45

Ile Phe Leu Phe Ile Leu Leu Leu Cys Leu Ile Phe Leu Leu Val Leu
     50                  55                  60

Leu Asp Tyr Gln Gly Met Leu Pro Val Cys Pro Leu Ile Pro Gly Ser
 65                  70                  75                  80

Ser Thr Thr Ser Thr Gly Pro Cys Arg Thr Cys Met Thr Thr Ala Gln
                 85                  90                  95

Gly Thr Ser Met Tyr Pro Ser Cys Cys Cys Thr Lys Pro Ser Asp Gly
            100                 105                 110

Asn Cys Thr Cys Ile Pro Ile Pro Ser Ser Trp Ala Phe Gly Lys Phe
        115                 120                 125

Leu Trp Glu Trp Ala Ser Ala Arg Phe Ser Trp Leu Ser Leu Leu Val
    130                 135                 140

Pro Phe Val Gln Trp Phe Val Gly Leu Ser
145                 150


<210> SEQ ID NO 12
<211> LENGTH: 154
<212> TYPE: PRT
<213> ORGANISM: Hepatitis B virus

<400> SEQUENCE: 12

Ser Trp Trp Thr Ser Leu Asn Phe Leu Gly Gly Thr Thr Val Cys Leu
  1               5                  10                  15

Gly Gln Asn Ser Gln Ser Pro Ile Ser Asn His Ser Pro Thr Ser Cys
             20                  25                  30

Pro Pro Thr Cys Pro Gly Tyr Arg Trp Met Cys Leu Arg Arg Phe Ile
         35                  40                  45

Ile Phe Leu Phe Ile Leu Leu Leu Cys Leu Ile Phe Leu Leu Val Leu
     50                  55                  60

Leu Asp Tyr Gln Gly Met Leu Pro Val Cys Pro Leu Ile Pro Gly Ser
 65                  70                  75                  80

Ser Thr Thr Ser Thr Gly Ser Cys Arg Thr Cys Thr Thr Pro Ala Gln
                 85                  90                  95

Gly Ile Ser Met Tyr Pro Ser Cys Cys Cys Thr Lys Pro Ser Asp Gly
            100                 105                 110

Asn Cys Thr Cys Ile Pro Ile Pro Ser Ser Trp Ala Phe Gly Lys Phe
        115                 120                 125

Leu Trp Glu Trp Ala Ser Ala Arg Phe Ser Trp Leu Ser Leu Leu Val
    130                 135                 140
```

-continued

```
Pro Phe Val Gln Trp Phe Val Gly Leu Ser
145                 150


<210> SEQ ID NO 13
<211> LENGTH: 154
<212> TYPE: PRT
<213> ORGANISM: Hepatitis B virus

<400> SEQUENCE: 13

Ser Trp Trp Thr Ser Leu Asn Phe Leu Gly Gly Thr Pro Val Cys Leu
  1             5                  10                  15

Gly Gln Asn Ser Gln Ser Gln Ile Ser Ser His Ser Pro Thr Cys Cys
             20                  25                  30

Pro Pro Ile Cys Pro Gly Tyr Arg Trp Met Cys Leu Arg Arg Phe Ile
         35                  40                  45

Ile Phe Leu Cys Ile Leu Leu Leu Cys Leu Ile Phe Leu Leu Val Leu
     50                  55                  60

Leu Asp Tyr Gln Gly Met Leu Pro Val Cys Pro Leu Ile Leu Gly Ser
 65                  70                  75                  80

Ser Thr Thr Ser Thr Gly Pro Cys Lys Thr Cys Thr Thr Pro Ala Gln
                 85                  90                  95

Gly Thr Ser Met Phe Pro Ser Cys Cys Cys Thr Lys Pro Thr Asp Gly
            100                 105                 110

Asn Cys Thr Cys Ile Pro Ile Pro Ser Ser Trp Ala Phe Ala Lys Tyr
        115                 120                 125

Leu Trp Glu Trp Ala Ser Val Arg Phe Ser Trp Leu Ser Leu Leu Val
    130                 135                 140

Pro Phe Val Gln Trp Phe Val Gly Leu Ser
145                 150


<210> SEQ ID NO 14
<211> LENGTH: 154
<212> TYPE: PRT
<213> ORGANISM: Hepatitis B virus

<400> SEQUENCE: 14

Ser Trp Trp Thr Ser Leu Asn Phe Leu Gly Gly Thr Pro Val Cys Leu
  1             5                  10                  15

Gly Gln Asn Ser Gln Ser Gln Ile Ser Ser His Ser Pro Thr Cys Cys
             20                  25                  30

Pro Pro Ile Cys Pro Gly Tyr Arg Trp Met Cys Leu Arg Arg Phe Ile
         35                  40                  45

Ile Phe Leu Cys Ile Leu Leu Leu Cys Leu Ile Phe Leu Leu Val Leu
     50                  55                  60

Leu Asp Tyr Gln Gly Met Leu Pro Val Cys Pro Leu Ile Leu Gly Ser
 65                  70                  75                  80

Ser Thr Thr Ser Thr Gly Pro Cys Lys Thr Cys Thr Thr Pro Ala Gln
                 85                  90                  95

Gly Thr Ser Met Phe Pro Ser Cys Cys Cys Thr Lys Pro Thr Asp Gly
            100                 105                 110

Asn Cys Thr Cys Ile Pro Ile Pro Ser Ser Trp Ala Phe Ala Lys Tyr
        115                 120                 125

Leu Trp Glu Trp Ala Ser Val Arg Phe Ser Trp Leu Ser Leu Leu Val
    130                 135                 140

Pro Phe Val Gln Trp Phe Val Gly Leu Ser
145                 150
```

-continued

<210> SEQ ID NO 15
<211> LENGTH: 154
<212> TYPE: PRT
<213> ORGANISM: Hepatitis B virus

<400> SEQUENCE: 15

```
Ser Trp Trp Thr Ser Leu Asn Phe Leu Gly Gly Thr Pro Val Cys Leu
  1               5                  10                  15

Gly Gln Asn Ser Gln Ser Gln Ile Ser Ser His Ser Pro Thr Cys Cys
             20                  25                  30

Pro Pro Ile Cys Pro Gly Tyr Arg Trp Met Cys Leu Arg Arg Phe Ile
         35                  40                  45

Ile Phe Leu Cys Ile Leu Leu Leu Cys Leu Ile Phe Leu Leu Val Leu
     50                  55                  60

Leu Asp Tyr Gln Gly Met Leu Pro Val Cys Pro Leu Ile Pro Gly Ser
 65                  70                  75                  80

Ser Thr Thr Ser Thr Gly Pro Cys Lys Thr Cys Thr Thr Pro Ala Gln
                 85                  90                  95

Gly Thr Ser Met Phe Pro Ser Cys Cys Cys Thr Lys Pro Thr Asp Gly
            100                 105                 110

Asn Cys Thr Cys Ile Pro Ile Pro Ser Ser Trp Ala Phe Ala Lys Tyr
        115                 120                 125

Leu Trp Glu Trp Ala Ser Val Arg Phe Ser Trp Leu Ser Leu Leu Val
    130                 135                 140

Pro Phe Val Gln Trp Phe Val Gly Leu Ser
145                 150
```

<210> SEQ ID NO 16
<211> LENGTH: 154
<212> TYPE: PRT
<213> ORGANISM: Hepatitis B virus

<400> SEQUENCE: 16

```
Ser Trp Trp Thr Ser Leu Ser Phe Leu Gly Gly Thr Pro Val Cys Leu
  1               5                  10                  15

Gly Gln Asn Ser Gln Ser Gln Ile Ser Ser His Ser Pro Thr Cys Cys
             20                  25                  30

Pro Pro Ile Cys Pro Gly Tyr Arg Trp Met Cys Leu Arg Arg Phe Ile
         35                  40                  45

Ile Phe Leu Cys Ile Leu Leu Leu Cys Leu Ile Phe Leu Leu Val Leu
     50                  55                  60

Leu Asp Tyr Gln Gly Met Leu Pro Val Cys Pro Leu Ile Pro Gly Ser
 65                  70                  75                  80

Ser Thr Thr Ser Thr Gly Pro Cys Lys Thr Cys Thr Thr Pro Ala Gln
                 85                  90                  95

Gly Thr Ser Met Phe Pro Ser Cys Cys Cys Thr Lys Pro Thr Asp Gly
            100                 105                 110

Asn Cys Thr Cys Ile Pro Ile Pro Ser Ser Trp Ala Phe Ala Lys Tyr
        115                 120                 125

Leu Trp Glu Trp Ala Ser Val Arg Phe Ser Trp Leu Ser Leu Leu Val
    130                 135                 140

Pro Phe Val Gln Trp Phe Val Gly Leu Ser
145                 150
```

<210> SEQ ID NO 17
<211> LENGTH: 154
<212> TYPE: PRT

-continued

<213> ORGANISM: Hepatitis B virus

<400> SEQUENCE: 17

```
Ser Trp Trp Thr Ser Leu Asn Phe Leu Gly Gly Thr Pro Val Cys Leu
  1               5                  10                  15

Gly Gln Asn Ser Gln Ser Gln Ile Ser Ser His Ser Pro Thr Cys Cys
             20                  25                  30

Pro Pro Ile Cys Pro Gly Tyr Arg Trp Met Cys Leu Arg Arg Phe Ile
         35                  40                  45

Ile Phe Leu Cys Ile Leu Leu Leu Cys Leu Ile Phe Leu Leu Val Leu
     50                  55                  60

Leu Asp Tyr Gln Gly Met Leu Pro Val Cys Pro Leu Ile Pro Gly Ser
 65                  70                  75                  80

Ser Thr Thr Ser Thr Gly Pro Cys Lys Ile Cys Thr Thr Pro Ala Gln
                 85                  90                  95

Gly Thr Ser Met Phe Pro Ser Cys Cys Cys Thr Lys Pro Thr Asp Gly
            100                 105                 110

Asn Cys Thr Cys Ile Pro Ile Pro Ser Ser Trp Ala Phe Ala Lys Tyr
        115                 120                 125

Leu Trp Glu Trp Ala Ser Val Arg Phe Ser Trp Leu Ser Leu Leu Val
    130                 135                 140

Pro Phe Val Gln Trp Phe Val Gly Leu Ser
145                 150
```

<210> SEQ ID NO 18
<211> LENGTH: 154
<212> TYPE: PRT
<213> ORGANISM: Hepatitis B virus

<400> SEQUENCE: 18

```
Ser Trp Trp Thr Ser Leu Asn Phe Leu Gly Gly Thr Pro Val Cys Leu
  1               5                  10                  15

Gly Gln Asn Ser Gln Ser Gln Ile Ser Ser His Ser Pro Thr Cys Cys
             20                  25                  30

Pro Pro Ile Cys Pro Gly Tyr Arg Trp Met Cys Leu Arg Arg Phe Ile
         35                  40                  45

Ile Phe Leu Cys Ile Leu Leu Leu Cys Leu Ile Phe Leu Leu Val Leu
     50                  55                  60

Leu Asp Tyr Gln Gly Met Leu Pro Val Cys Pro Leu Ile Pro Gly Ser
 65                  70                  75                  80

Ser Thr Thr Ser Thr Gly Pro Cys Lys Thr Cys Thr Thr Pro Ala Gln
                 85                  90                  95

Gly Thr Ser Met Phe Pro Ser Cys Cys Cys Thr Lys Pro Met Asp Gly
            100                 105                 110

Asn Cys Thr Cys Ile Pro Ile Pro Ser Ser Trp Ala Phe Ala Lys Tyr
        115                 120                 125

Leu Trp Glu Trp Ala Ser Val Arg Phe Ser Trp Leu Ser Leu Leu Val
    130                 135                 140

Pro Phe Val Gln Trp Phe Val Gly Leu Ser
145                 150
```

<210> SEQ ID NO 19
<211> LENGTH: 154
<212> TYPE: PRT
<213> ORGANISM: Hepatitis B virus -continued

<400> SEQUENCE: 19

Ser Trp Trp Thr Ser Leu Asn Phe Ile Gly Gly Ser Pro Val Cys Leu
1 5 10 15

Gly Gln Asn Ser Gln Ser Pro Thr Ser Asn His Ser Pro Thr Ser Cys
20 25 30

Pro Pro Ile Cys Pro Gly Tyr Arg Trp Met Cys Leu Arg Arg Phe Ile
35 40 45

Ile Phe Leu Phe Ile Leu Leu Leu Cys Leu Ile Phe Leu Leu Val Leu
50 55 60

Leu Asp Tyr Gln Gly Met Leu Pro Val Cys Pro Leu Ile Pro Gly Ser
65 70 75 80

Thr Thr Thr Ser Thr Gly Pro Cys Lys Thr Cys Thr Thr Pro Ala Gln
85 90 95

Gly Asn Ser Met Phe Pro Ser Cys Cys Cys Thr Lys Pro Thr Val Gly
100 105 110

Asn Cys Thr Cys Ile Pro Ile Pro Ser Ser Trp Ala Phe Ala Lys Tyr
115 120 125

Leu Trp Glu Trp Ala Ser Val Arg Phe Ser Trp Leu Ser Leu Leu Val
130 135 140

Pro Phe Val Gln Trp Phe Val Gly Leu Ser
145 150

<210> SEQ ID NO 20
<211> LENGTH: 154
<212> TYPE: PRT
<213> ORGANISM: Hepatitis B virus

<400> SEQUENCE: 20

Ser Trp Trp Thr Ser Leu Asn Phe Leu Gly Gly Ser Pro Val Cys Leu
1 5 10 15

Gly Gln Asn Ser Arg Ser Pro Thr Ser Asn His Ser Pro Thr Ser Cys
20 25 30

Pro Pro Ile Cys Pro Gly Tyr Arg Trp Met Cys Leu Arg Arg Phe Ile
35 40 45

Ile Phe Leu Phe Ile Leu Leu Leu Cys Leu Ile Phe Leu Leu Val Leu
50 55 60

Leu Asp Tyr Gln Gly Met Leu Pro Val Cys Pro Leu Ile Leu Gly Ser
65 70 75 80

Thr Thr Thr Ser Thr Gly Pro Cys Lys Thr Cys Thr Thr Pro Ala Gln
85 90 95

Gly Asn Ser Met Phe Pro Ser Cys Cys Cys Thr Lys Pro Thr Asp Gly
100 105 110

Asn Cys Thr Cys Ile Pro Ile Pro Ser Ser Trp Ala Phe Ala Lys Tyr
115 120 125

Leu Trp Glu Trp Ala Ser Val Arg Phe Ser Trp Leu Ser Leu Leu Val
130 135 140

Pro Phe Val Gln Trp Phe Val Gly Leu Ser
145 150

<210> SEQ ID NO 21
<211> LENGTH: 154
<212> TYPE: PRT
<213> ORGANISM: Hepatitis B virus -continued

<400> SEQUENCE: 21

```
Ser Trp Trp Thr Ser Leu Asn Phe Leu Gly Gly Ser Pro Val Cys Leu
  1               5                  10                  15

Gly Gln Asn Ser Gln Ser Pro Thr Ser Asn His Ser Pro Thr Ser Cys
             20                  25                  30

Pro Pro Ile Cys Pro Gly Tyr Arg Trp Met Cys Leu Arg Arg Phe Ile
         35                  40                  45

Ile Phe Leu Phe Ile Leu Leu Leu Cys Leu Ile Phe Leu Leu Val Leu
     50                  55                  60

Leu Asp Tyr Gln Gly Met Leu Pro Val Cys Pro Ile Ile Pro Gly Ser
 65                  70                  75                  80

Thr Thr Thr Ser Thr Gly Pro Cys Lys Thr Cys Thr Thr Pro Ala Gln
                 85                  90                  95

Gly Asn Ser Leu Phe Pro Ser Cys Cys Cys Thr Lys Pro Thr Asp Gly
            100                 105                 110

Asn Cys Thr Cys Ile Pro Ile Pro Ser Ser Trp Ala Phe Ala Lys Tyr
        115                 120                 125

Leu Trp Glu Arg Ala Ser Val Arg Phe Ser Trp Leu Ser Leu Leu Val
    130                 135                 140

Pro Phe Val Gln Trp Phe Val Gly Leu Ser
145                 150
```

<210> SEQ ID NO 22
<211> LENGTH: 154
<212> TYPE: PRT
<213> ORGANISM: Hepatitis B virus

<400> SEQUENCE: 22

```
Ser Trp Trp Thr Ser Leu Asn Phe Leu Gly Gly Ala Pro Thr Cys Pro
  1               5                  10                  15

Gly Gln Asn Ser Gln Ser Pro Thr Ser Asn His Ser Pro Thr Ser Cys
             20                  25                  30

Pro Pro Ile Cys Pro Gly Tyr Arg Trp Met Cys Leu Arg Arg Phe Ile
         35                  40                  45

Ile Phe Leu Phe Ile Leu Leu Leu Cys Leu Ile Phe Leu Leu Val Leu
     50                  55                  60

Leu Asp Tyr Gln Gly Met Leu Pro Val Cys Pro Leu Leu Pro Gly Thr
 65                  70                  75                  80

Ser Thr Thr Ser Thr Gly Pro Cys Lys Thr Cys Thr Ile Pro Ala Gln
                 85                  90                  95

Gly Thr Ser Met Phe Pro Ser Cys Cys Cys Thr Lys Pro Ser Asp Gly
            100                 105                 110

Asn Cys Thr Cys Ile Pro Ile Pro Ser Ser Trp Ala Phe Ala Arg Phe
        115                 120                 125

Leu Trp Glu Gly Ala Ser Val Arg Phe Ser Trp Leu Ser Leu Leu Val
    130                 135                 140

Pro Phe Val Gln Trp Phe Val Gly Leu Ser
145                 150
```

<210> SEQ ID NO 23
<211> LENGTH: 154
<212> TYPE: PRT
<213> ORGANISM: Hepatitis B virus -continued

<400> SEQUENCE: 23

```
Ser Trp Trp Thr Ser Leu Asn Phe Leu Gly Gly Ala Pro Thr Cys Pro
  1               5                  10                  15

Gly Gln Asn Ser Gln Ser Pro Thr Ser Asn His Ser Pro Thr Ser Cys
             20                  25                  30

Pro Pro Thr Cys Pro Gly Tyr Arg Trp Met Cys Leu Arg Arg Phe Ile
         35                  40                  45

Ile Phe Leu Phe Ile Leu Leu Leu Cys Leu Ile Phe Leu Leu Val Leu
     50                  55                  60

Leu Asp Tyr Gln Gly Met Leu Pro Val Cys Pro Leu Leu Pro Gly Thr
 65                  70                  75                  80

Ser Thr Thr Ser Thr Gly Pro Cys Lys Thr Cys Thr Ile Pro Ala Gln
                 85                  90                  95

Gly Thr Ser Met Phe Pro Ser Cys Cys Cys Thr Lys Pro Ser Asp Gly
            100                 105                 110

Asn Cys Thr Cys Ile Pro Ile Pro Ser Ser Trp Ala Phe Ala Arg Phe
        115                 120                 125

Leu Trp Glu Trp Ala Ser Val Arg Phe Ser Trp Leu Ser Leu Leu Val
    130                 135                 140

Pro Phe Val Gln Trp Phe Val Gly Leu Ser
145                 150
```

<210> SEQ ID NO 24
<211> LENGTH: 154
<212> TYPE: PRT
<213> ORGANISM: Hepatitis B virus

<400> SEQUENCE: 24

```
Ser Trp Trp Thr Ser Leu Asn Phe Leu Gly Glu Ala Pro Thr Cys Pro
  1               5                  10                  15

Gly Gln Asn Ser Gln Ser Pro Thr Ser Asn His Ser Pro Thr Ser Cys
             20                  25                  30

Pro Pro Ile Cys Pro Gly Tyr Arg Trp Met Cys Leu Arg Arg Phe Ile
         35                  40                  45

Ile Phe Leu Phe Ile Leu Leu Leu Cys Leu Ile Phe Leu Leu Val Leu
     50                  55                  60

Leu Asp Tyr Gln Gly Met Leu Pro Val Cys Pro Leu Leu Pro Gly Thr
 65                  70                  75                  80

Ser Thr Thr Ser Thr Gly Pro Cys Lys Thr Cys Thr Ile Pro Ala Gln
                 85                  90                  95

Gly Thr Ser Met Phe Pro Ser Cys Cys Cys Thr Lys Pro Ser Asp Gly
            100                 105                 110

Asn Cys Thr Cys Ile Pro Ile Pro Ser Ser Trp Ala Phe Ala Arg Phe
        115                 120                 125

Leu Trp Glu Trp Ala Ser Val Arg Phe Ser Trp Leu Ser Leu Leu Val
    130                 135                 140

Pro Phe Val Gln Trp Phe Ala Gly Leu Ser
145                 150
```

<210> SEQ ID NO 25
<211> LENGTH: 154
<212> TYPE: PRT
<213> ORGANISM: Hepatitis B virus -continued

```
<400> SEQUENCE: 25

Ser Trp Trp Thr Ser Leu Asn Phe Leu Gly Gly Ala Pro Thr Cys Pro
  1               5                  10                  15

Gly Arg Asn Ser Gln Ser Pro Thr Ser Asn His Ser Pro Thr Ser Cys
             20                  25                  30

Pro Pro Ile Cys Pro Gly Tyr Arg Trp Met Cys Leu Arg Arg Phe Ile
         35                  40                  45

Ile Phe Leu Phe Ile Leu Leu Leu Cys Leu Ile Phe Leu Leu Val Leu
     50                  55                  60

Leu Asp Tyr Gln Gly Met Leu Pro Val Cys Pro Leu Leu Pro Gly Thr
 65                  70                  75                  80

Ser Thr Thr Ser Thr Gly Pro Cys Lys Thr Cys Thr Thr Pro Ala Gln
                 85                  90                  95

Gly Asn Ser Met Phe Pro Ser Cys Cys Cys Thr Lys Pro Ser Asp Gly
            100                 105                 110

Asn Cys Thr Cys Ile Pro Ile Pro Ser Ser Trp Ala Phe Ala Arg Phe
        115                 120                 125

Leu Trp Glu Trp Ala Ser Val Arg Phe Ser Trp Leu Ser Leu Leu Val
    130                 135                 140

Pro Phe Val Gln Trp Phe Val Gly Leu Ser
145                 150


<210> SEQ ID NO 26
<211> LENGTH: 154
<212> TYPE: PRT
<213> ORGANISM: Hepatitis B virus

<400> SEQUENCE: 26

Ser Trp Trp Thr Ser Leu Asn Phe Leu Gly Gly Leu Pro Gly Cys Pro
  1               5                  10                  15

Gly Gln Asn Ser Gln Ser Pro Thr Ser Asn His Leu Pro Thr Ser Cys
             20                  25                  30

Pro Pro Thr Cys Pro Gly Tyr Arg Trp Met Cys Leu Arg Arg Phe Ile
         35                  40                  45

Ile Phe Leu Phe Ile Leu Leu Leu Cys Leu Ile Phe Leu Leu Val Leu
     50                  55                  60

Leu Asp Tyr Gln Gly Met Leu Pro Val Cys Pro Leu Leu Pro Gly Ser
 65                  70                  75                  80

Thr Thr Thr Ser Thr Gly Pro Cys Lys Thr Cys Thr Thr Leu Ala Gln
                 85                  90                  95

Gly Thr Ser Met Phe Pro Ser Cys Cys Cys Ser Lys Pro Ser Asp Gly
            100                 105                 110

Asn Cys Thr Cys Ile Pro Ile Pro Ser Ser Trp Ala Leu Gly Lys Tyr
        115                 120                 125

Leu Trp Glu Trp Ala Ser Ala Arg Phe Ser Trp Leu Ser Leu Leu Val
    130                 135                 140

Gln Phe Val Gln Trp Cys Val Gly Leu Ser
145                 150


<210> SEQ ID NO 27
<211> LENGTH: 154
<212> TYPE: PRT
<213> ORGANISM: Hepatitis B virus
```

-continued

<400> SEQUENCE: 27

```
Ser Trp Trp Thr Ser Leu Asn Phe Leu Gly Gly Thr Thr Val Cys Leu
  1               5                  10                  15

Gly Gln Asn Ser Gln Ser Pro Thr Ser Asn His Ser Pro Thr Ser Cys
             20                  25                  30

Pro Pro Thr Cys Pro Gly Tyr Arg Trp Met Cys Leu Arg Arg Phe Ile
         35                  40                  45

Ile Phe Leu Phe Ile Leu Leu Leu Cys Leu Ile Phe Leu Leu Ala Leu
     50                  55                  60

Leu Asp Tyr Gln Gly Met Leu Pro Val Cys Pro Leu Ile Pro Gly Leu
 65                  70                  75                  80

Ser Thr Thr Arg Thr Gly Ala Tyr Gln Pro Cys Thr Thr Ile Ala Gln
                 85                  90                  95

Gly Thr Ser Thr Tyr Pro Ser Cys Cys Cys Ile Lys Pro Ser Asp Gly
            100                 105                 110

Asn Tyr Thr Tyr Ile Pro Ile Pro Ser Ser Trp Ala Phe Gly Lys Phe
        115                 120                 125

Leu Trp Glu Trp Ala Ser Ala Arg Phe Ser Trp Leu Ser Leu Leu Val
    130                 135                 140

Pro Phe Val Gln Trp Phe Ala Gly Leu Ser
145                 150
```

<210> SEQ ID NO 28
<211> LENGTH: 7
<212> TYPE: PRT
<213> ORGANISM: Hepatitis B virus

<400> SEQUENCE: 28

```
Arg Thr Gly Ala Tyr Gln Pro
  1               5
```

<210> SEQ ID NO 29
<211> LENGTH: 21
<212> TYPE: PRT
<213> ORGANISM: Hepatitis B virus

<400> SEQUENCE: 29

```
Leu Ser Thr Ile Arg Thr Gly Ala Tyr Gln Pro Cys Thr Thr Ile Ala
  1               5                  10                  15

Gln Gly Thr Ser Thr
             20
```

<210> SEQ ID NO 30
<211> LENGTH: 10
<212> TYPE: PRT
<213> ORGANISM: Hepatitis B virus

<400> SEQUENCE: 30

```
Ile Lys Pro Ser Asp Gly Asn Tyr Thr Tyr
  1               5                  10
```

<210> SEQ ID NO 31
<211> LENGTH: 33
<212> TYPE: PRT
<213> ORGANISM: Hepatitis B virus

<400> SEQUENCE: 31

```
Arg Thr Gly Ala Tyr Gln Pro Cys Thr Thr Ile Ala Gln Gly Thr Ser
  1               5                  10                  15
```

-continued

```
Thr Tyr Pro Ser Cys Cys Cys Ile Lys Pro Ser Asp Gly Asn Tyr Thr
             20                  25                  30

Tyr


<210> SEQ ID NO 32
<211> LENGTH: 24
<212> TYPE: DNA
<213> ORGANISM: Hepatitis B virus

<400> SEQUENCE: 32

ctcgtggtgg acttctctca attt                                            24


<210> SEQ ID NO 33
<211> LENGTH: 21
<212> TYPE: DNA
<213> ORGANISM: Hepatitis B virus

<400> SEQUENCE: 33

ggaaagccct acgaaccact g                                               21


<210> SEQ ID NO 34
<211> LENGTH: 36
<212> TYPE: DNA
<213> ORGANISM: Hepatitis B virus

<400> SEQUENCE: 34

ggaytmtcga ccatcmgcac gggagcatac caaccc                               36


<210> SEQ ID NO 35
<211> LENGTH: 36
<212> TYPE: DNA
<213> ORGANISM: Hepatitis B virus

<400> SEQUENCE: 35

gggttggtat gctcccgtgc kgatggtcga kartcc                               36


<210> SEQ ID NO 36
<211> LENGTH: 24
<212> TYPE: DNA
<213> ORGANISM: Hepatitis B virus

<400> SEQUENCE: 36

accatcmgca cgggagcata ccaa                                            24


<210> SEQ ID NO 37
<211> LENGTH: 24
<212> TYPE: DNA
<213> ORGANISM: Hepatitis B virus

<400> SEQUENCE: 37

ttggtatgct cccgtgckga tggt                                            24


<210> SEQ ID NO 38
<211> LENGTH: 24
<212> TYPE: DNA
<213> ORGANISM: Hepatitis B virus

<400> SEQUENCE: 38

ccaggaytmt cgaccatcmg cacg                                            24


<210> SEQ ID NO 39
<211> LENGTH: 24
<212> TYPE: DNA
```

-continued

```
<213> ORGANISM: Hepatitis B virus

<400> SEQUENCE: 39

tcccgtgckg atggtcgaka rtcc                                        24


<210> SEQ ID NO 40
<211> LENGTH: 25
<212> TYPE: DNA
<213> ORGANISM: Hepatitis B virus

<400> SEQUENCE: 40

gcataccaac cctgcacgac tattg                                       25


<210> SEQ ID NO 41
<211> LENGTH: 25
<212> TYPE: DNA
<213> ORGANISM: Hepatitis B virus

<400> SEQUENCE: 41

caatagtcgt gcagggttgg tatgc                                       25


<210> SEQ ID NO 42
<211> LENGTH: 33
<212> TYPE: DNA
<213> ORGANISM: Hepatitis B virus

<400> SEQUENCE: 42

gtatcaaacc ttcggacgga aattacacct ata                              33


<210> SEQ ID NO 43
<211> LENGTH: 22
<212> TYPE: DNA
<213> ORGANISM: Hepatitis B virus

<400> SEQUENCE: 43

tcggacggaa attacaccta ta                                          22


<210> SEQ ID NO 44
<211> LENGTH: 22
<212> TYPE: DNA
<213> ORGANISM: Hepatitis B virus

<400> SEQUENCE: 44

tgggatggga atataggtgt aa                                          22
```

ESCAPE MUTANT OF THE SURFACE ANTIGEN OF HEPATITIS B VIRUS

FIELD OF THE INVENTION

The present invention relates to an escape mutant of the surface antigen of the hepatitis B virus.

BACKGROUND OF THE INVENTION

Serum from patients infected with hepatitis B virus (HBV) commonly have three distinct structures that contain the hepatitis B surface antigen (HBsAg): Dane particles, spherical particles, and filamentous particles. Dane particles are spheres that are 42 nm in diameter with a core that is 28 nm in diameter. The spherical particles have a diameter of about 22 nm. Filamentous particles have a diameter of about 22 nm and a length from about 50 nm to about 230 nm.

The particles contain three glycoprotein designated the major, middle, and large proteins. The hepatitis B surface antigen open reading frame of HBV-DNA is divided into three regions, pre-S 1, pre-S2, and S. This open reading frame encodes the major, middle, and large proteins. The complete amino acid sequence for the major protein is given in Valenzuela et al., *Nature*, 280:815–819 (1979). The amino acid sequence in Valenzuela et al. is 226 amino acids long and the amino acid positions referred to in this application refer to the amino acid sequence disclosed in Valenzuela et al. HBsAg contains several antigenic determinant,;, the most important of these are the a determinant, the d/y determinant, and the w/r determinant.

Hepatitis B vaccines have been used (extensively in humans in recent years. A typical vaccine, e.g., RECOMBIVAX HB vaccine, available from Merck, contains HBsAg of the adw subtype that has been produced recombinantly in yeast. As the human population becomes vaccinated, the virus is put under pressure to evolve around the vaccine. Mutants that evolve in response to the vaccine are termed "escape mutants." Current vaccines may not be effective against these (escape mutants. Also, some current immunodiagnostic tests may not detect these escape mutants.

Certain HBV escape mutants have been reported previously. A mutation at position 145 from glycine to arginine was reported by Carman et al., *Lancet*, 336:325–329 (1990). Also, a mutation where additional amino acids were inserted after amino acid 122 was reported in WO 95/21189. Other mutants are described in McMahon et al., *Hepatology,* 15(5):757–766 (1992). In addition, studies have been conducted on artificial mutant proteins. An example of this type of study is Mazngold et al., *Virology*, 211:535–543 (1995). Mangolet et al. made various mutations at positions 121, 124, 137, 139, 147, and 149.

The invention provides isolated mutant hepatitis B surface antigen proteins, fragments thereof, and particles containing these proteins. These mutant proteins, fragments, and particles can be used in improved vaccines and these mutant proteins, fragments, and particles and specific binding agents to them can be used in improved immunoassays.

SUMMARY OF THE INVENTION

The invention provides an isolated mutant hepatitis B surface antigen protein which comprises an amino acid sequence of a surface antigen protein of hepatitis B virus which infects humans, in which the amino acid at position 121 is not cysteine and at least one of the amino acids at positions 120, 122, 123, 147, or 149 is not a conserved amino acid for its position. The invention also provides an isolated mutant hepatitis B surface antigen protein which comprises an amino acid sequence of a surface antigen protein of hepatitis B virus which infects humans, in which the amino acid at position 122 is not a conserved amino acid for its position.

The invention also provides a vaccine which comprises an immunogenic amount of a mutant hepatitis B surface antigen protein, a fragment thereof, or a particle containing the protein, in a pharmaceutically acceptable carrier. The invention also provides specific binding agents which specifically recognize a mutant hepatitis B surface antigen protein, a fragment thereof, or a particle containing the protein.

The invention also provides a method for detecting in a sample a mutant hepatitis B surface antigen protein or a particle containing the protein comprising: (a) contacting a sample with a specific binding agent which specifically recognizes a mutant surface antigen protein of the invention under conditions suitable for binding to occur; and (b) measuring the extent of the binding of the specific binding agent, wherein the extent of the binding correlates to the presence or amount of mutant hepatitis B surface antigen protein or a particle containing the protein in the sample; to determine the presence or amount of mutant hepatitis B surface antigen protein or a particle containing the protein in the sample. Method; for calibrating a method for determining the amount of a mutant hepatitis B surface antigen protein or a particle containing the protein, in a sample and for testing the binding affinity of a specific binding agent a mutant hepatitis B surface antigen protein, a fragment thereof, or a particle containing the protein, are also provided.

The invention provides a method of detecting in a sample a nucleic acid sequence coding for a mutant hepatitis B surface antigen protein comprising: (a) providing a sample suspected. of containing a nucleic acid sequence coding for a mutant hepatitis B surface antigen protein of the invention; and (b) detecting the nucleic acid sequence coding for the mutant hepatitis B surface antigen protein.

Additional features and advantages of the invention are set forth in the description which follows and in part will be apparent from the description. The objectives and other advantages of the invention will be realized and attained by the isolated mutant hepatitis B surface antigen proteins, fragments thereof, and particles containing these proteins, specific binding agents thereto, and immunoassays and vaccines using these proteins, fragments thereof, and particles containing these proteins and/or specific binding agents as particularly pointed out in the written description, claims, and appended drawings. It is to be understood that both the foregoing general description and the following detailed description are exemplary and explanatory and are intended to provide further explanation of the invention as claimed.

BRIEF DESCRIPTION OF THE DRAWINGS

FIG. 1 depicts the partial amino acid sequence of the CTS mutant hepatitis B surface antigen protein.

FIG. 2 compares the partial amino acid sequence of the CTS mutant hepatitis B surface antigen protein to some other HBV subtypes.

FIG. 3A–3E compares the partial amino acid sequence of the CTS mutant hepatitis B surface antigen protein to some other HBV subtype.

In FIGS. 6 to 8 the solid line and squares represent the antibody response to natural HBsAg and the dashed line and diamonds represent the antibody response to the mutant HBsAg.

DETAILED DESCRIPTION OF THE INVENTION

Figure 4:
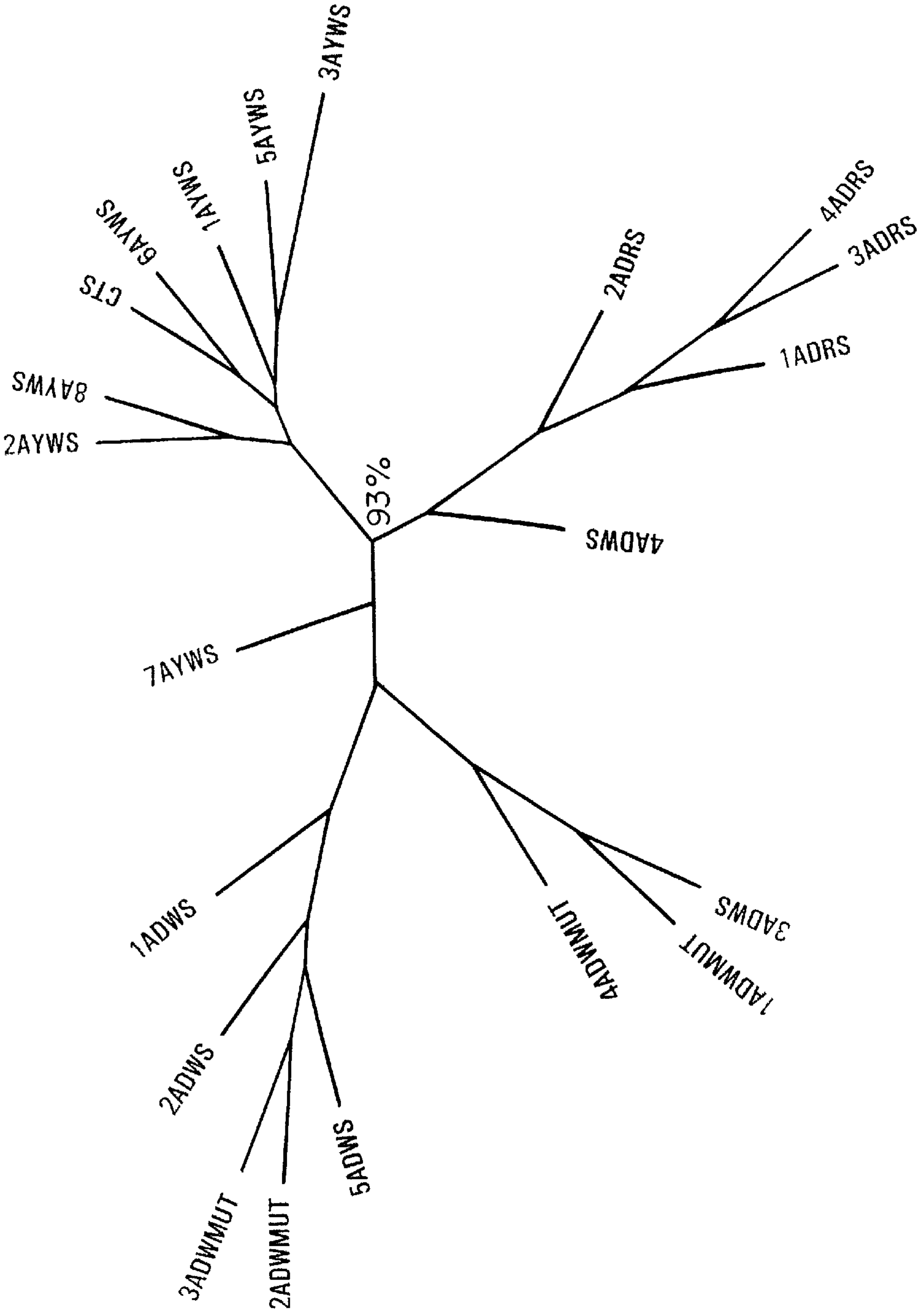
FIGS. 4 and 5 depict phylogenic subtype groupings and distances for the mutant HBsAg-CTS and for twenty subtypes of the Hepatitis B virus.

The invention provides an isolated mutant hepatitis B surface antigen protein which comprises an amino acid sequence of a surface antigen protein of hepatitis B virus which infects humans, in which the amino acid at position 121 is not cysteine and at least one of the amino acids at positions 120, 122, 123, 147, or 149 is not a conserved amino acid for its position. In one embodiment, the isolated mutant hepatitis B surface antigen protein displays an antigenicity different from that of wild-type hepatitis B surface antigen protein. In another embodiment, at least one of the amino acids at positions 120, 122, or 123 is not a conserved amino acid for its position; in still another embodiment, at least one of the amino acids at positions 147 or 149 is not a conserved amino acid for its position.

In one embodiment of the invention, at least two of the aimino acids at positions 120, 122, 123, 147, or 149 are not conserved amino acids for their positions. In other embodiments, at least three, at least four, or all five of the amino acids at positions 120, 122, 123, 147, or 149 are not conserved amino acids for their positions.

In other embodiments, the conserved cysteine at position 121 is replaced by tyrosine; the conserved proline; at position 120 is replaced by alanine; the conserved lysine or arginine at position 122 is replaced by glutamine; and/or the conserved threonine at position 123 is replaced by proline. In one embodiment, the conserved proline at position 120 is replaced by alanine, the conserved lysine or arginine at position 122 is replaced by glutamine, and the conserved threonine at position 123 is replaced by proline.

In another embodiment, the amino acid at position 127 is not a conserved amino acid for its position; preferably, the conserved proline at position 127 is replaced by isoleucine. In another embodiment, the amino acid at position 117 is not a conserved amino acid for its position; preferably, the conserved serine at position 117 is replaced by arginine. In another embodiment, the amino acid at position 96 is not a conserved amino acid for its position; preferably, the conserved valine at position 96 is replaced by alanine. In another embodiment, the amino acid at position 113 is not a conserved amino acid for its position; preferably, the conserved serine or threonine at position 113 is replaced by leucine.

In another embodiment, the amino acid at position 133 is not a conserved amino acid for its position; preferably, the conserved methionine at position 133 is replaced by threonine. In another embodiment, the amino acid at position 140 is not a conserved amino acid for its position; preferably, the conserved threonine at position 140 is replaced by isoleucine. In another embodiment, the amino acid at position 147 is not a conserved amino acid for its position; preferably, the conserved cysteine at position 147 is replaced by tyrosine. In another embodiment, the amino acid at position 149 is not a conserved amino acid for its position; preferably, the conserved cysteine at position 149 is replaced by tyrosine.

In another embodiment, the amino acids at positions 147 and 149 are not conserved amino acids for their positions. In another embodiment, the conserved cysteines at position 121, 147, and 149 are replaced by tyrosines. In still another embodiment, the amino acid at position 145 is the conserved glycine. In another embodiment, the amino acids at positions 137, 138, and 139 are all conserved cysteines. In another embodiment, the amino acid at position 124 is the conserved cysteine.

The invention provides an isolated mutant hepatitis B surface antigen protein which comprises an amino acid sequence of a surface antigen protein of hepatitis B virus which infects humans, in which the amino acid at position 122 is not a conserved amino acid for its position. In one embodiment, the isolated mutant hepatitis B surface antigen protein displays an antigenicity different from that of wild-type hepatitis B surface antigen protein. In another embodiment, the conserved lysine or arginine at position 122 is replaced by glutamine.

In embodiments of the invention, the isolated mutant hepatitis B surface antigen protein is the major protein of hepatitis B surface antigen, the middle protein of hepatitis B surface antigen, the large protein of hepatitis B surface antigen. In another embodiment of the invention the protein includes a pre-S sequence. In other embodiments of the invention the protein includes a portion of or a complete pre-S1 sequence or a portion of or a complete pre-S2 sequence.

In one embodiment of the invention, the isolated mutant hepatitis B surface antigen protein comprises the following sequence of amino acids at positions 117 to 123: Arg-Thr-Gly-Ala-Tyr-Gln-Pro (SEQ ID NO: 28). In another embodiment, the isolated mutant hepatitis B surface antigen protein comprises the following sequence of amino acids at positions 113 to 133: Leu-Ser-Thr-Ile-Arg-Thr-Gly-Ala-Tyr-Gln-Pro-Cys-Thr-Thr-Ile-Ala-Gln-Gly-Thr-Ser-Thr (SEQ ID NO:29). In another embodiment, the isolated mutant hepatitis B surface antigen protein comprises the following sequence of amino acids at positions 140 to 147: Ile-Lys-Pro-Ser-Asp-Gly-Asn-Tyr-Thr-Tyr (SEQ ID NO:30). In one embodiment, the isolated mutant hepatitis B surface antigen protein comprises the following sequence of amino acids at positions 117 to 123: Arg-Thr-Gly-Aka-Tyr-Gln-Pro (SEQ ID NO:28) and the following sequence of amino acids at positions 140 to 147: Ile-Lys-Pro-Ser-Asp-Gly-Asn-Tyr-Thr-Tyr (SEQ ID NO:30). In another embodiment, the isolated mutant hepatitis B surface antigen protein comprises the following sequence of amino acids at positions 117 to 149: Arg-Thr-Gly-Ala-Tyr-Gln-Pro-Cys-Thr-Thr-Ile-Ala-Gln-Gly-Thr-Ser-Thr-Tyr-Pro-Ser-Cys-Cys-Cys-Ile-Lys-Pro-Ser-Asp-Gly-Asn-Tyr-Thr-Tyr (SEQ ID NO:31). In another embodiment, the isolated mutant hepatitis B surface antigen protein comprises the sequence of amino acids listed in SEQ ID NO:2 (see below).

The invention provides an isolated mutant hepatitis B particle which comprises a mutant hepatitis B surface antigen protein of the invention. The invention also provides fragments of mn isolated mutant hepatitis B surface antigen protein of the invention. When used in this application, a "fragment" of a mutant hepatitis B surface antigen protein means a fragment that comprises a sequence of at least thirty amino acids containing the sequence of amino acids at positions 120 to 149). A preferred fragment is an isolated fragment of a mutant hepatitis B surface antigen protein in which the isolated fragment comprises a sequence of at least thirty amino acids, said sequence comprising the amino acids at positions 120 to 149, in which the amino acid at position 121 is not cysteine and at least one of the amino acids at positions 120, 122, 123, 147, or 149 is not a conserved amino acid for its position. Another preferred fragment is an isolated fragment of a mutant hepatitis B surface antigen protein in which the isolated fragment comprises a sequence of at least thirty amino acids, said sequence comprising the amino acids at positions 120 to 149, in which the amino acid at position 122 is not a conserved amino acid for its position.

The invention also provides a composition which comprises a mutant hepatitis B surface antigen protein of the invention, a fragment thereof, or a particle containing the protein, and is substantially blood-free.

The invention provides a vaccine which comprises an immunogenic amount of a mutant hepatitis B surface antigen protein of the invention, a fragment thereof, or a particle containing the protein, in a pharmaceutically acceptable carrier.

The invention provides a specific binding agent which specifically recognizes a mutant hepatitis B surface antigen protein of the invention, a fragment thereof, or a particle containing the protein, wherein the specific binding agent was specifically raised against the mutant hepatitis, B surface antigen protein, a fragment thereof, or a particle containing the protein. In one embodiment, the specific binding agent does not substantially bind native HBV with any of the following phenotypes: ayw, Ur, adr, or adw. In another embodiment, the specific binding agent substantially binds native HBV with any of the following phenotypes: ayw, ayr, adr, or adw. In one embodiment the specific binding agent recognizes a sequential epitope; in another embodiment the specific binding agent recognizes a conformational epitope. The specific binding agent may be a monoclonal antibody, a fragmentary monoclonal antibody, or a polyclonal antibody.

The invention provides a secreting hybridoma of a monoclonal antibody of the invention.

The invention provides a control sample comprising a known amount of a mutant hepatitis B surface antigen protein, a fragment thereof, or a particle containing the protein.

The invention provides a method for detecting in a sample a mutant hepatitis B surface antigen protein or a particle containing the protein comprising: (a) contacting a sample with at specific binding agent which specifically recognizes a mutant surface antigen protein of the invention under conditions suitable for binding to occur; and (b) measuring the extent of the binding of the specific binding agent, wherein the extent of the binding correlates to the presence or amount of mutant hepatitis B surface antigen protein or a particle containing the protein in the sample; to determine the presence or amount of mutant hepatitis B surface antigen protein or a particle containing the protein in the sample. In one embodiment, the correlation between the extent of the binding and the presence or amount of mutant hepatitis B surface antigen protein or a particle containing the protein in the sample has been determined using control samples containing known amounts of the mutant hepatitis B surface antigen protein, a fragment thereof, or a particle containing the protein. In another embodiment, the specific binding agent was specifically raised against the mutant hepatitis B surface antigen protein or a particle containing the protein. In another embodiment, the method comprises a non-competitive assay. In still another embodiment, the assay comprises a second specific binding agent w which has a label; the label can be a radioactive label, an enzyme label, a fluorescent label, a chemiluminescent label, a bioluminescent label, or an epifluorescent label. In another embodiment, the method comprises an agglutination assay; in still another embodiment, the method comprises a competitive assay. The method can comprise using a labeled substrate that cross-reacts with the mutant hepatitis B surface antigen protein or particle containing the protein. The sample can be a blood sample or a vaccine.

The invention provides a method for calibrating an assay for a mutant hepatitis B surface antigen protein or a particle containing the protein comprising: (a) providing two or more control samples comprising known amounts of a mutant hepatitis B surface antigen protein of the invention, a fragment thereof, or a particle containing the protein; (b) testing each of the control samples in the assay and recording the signal that each control sample produced; and (c) producing a calibration curve that correlates the signal produced with the amount of mutant hepatitis B surface antigen protein, the fragment thereof, or the particle containing the protein in a sample.

The invention provides a method of testing the binding affinity of a specific binding agent comprising: (a) providing a control sample comprising a known amount of a mutant hepatitis B surface antigen protein of the invention, a fragment thereof, or a particle containing the protein; (b) contacting the control sample with a specific binding agent under conditions suitable for binding to occur; and (c) measuring the extent of the binding of the specific binding agent; to determine the binding affinity of the specific binding agent to the mutant hepatitis B surface antigen protein, the fragment thereof, or the particle containing the protein. In one embodiment, the binding affinity is compared with a predetermined minimum value for the binding affinity. In another embodiment, this comparison is part of a quality control procedure for producing a diagnostic immunoassay kit. In a preferred embodiment, the specific binding agent is a monoclonal antibody or a fragmentary monoclonal antibody.

The invention provides a diagnostic immunoassay kit comprising a specific binding agent of the invention. The invention also provides a diagnostic immunoassay kit comprising a control sample of the invention.

The invention provides a mutant hepatitis B surface antigen protein of the invention, a fragment thereof, or a particle containing the protein, which has been recombinantly produced. In one embodiment, the protein, particle, or fragment has been recombinantly produced in a yeast, bacterium, or mammalian cell.

The invention provides isolated DNA which codes for a mutant hepatitis B surface antigen protein of the invention, a fragment thereof, or a particle containing the protein. In one embodiment, the isolated DNA comprises a sequence which codes for the amino acid sequence of SEQ ID NO: 2. In another embodiment, the isolated DNA comprises a sequence which codes for the following amino acid sequence: Arg-Thr-Gly-Ala-Tyr-Gln-Pro-Cys-Thr-Thr-Ile-Ala-Gln-Gly-Thr-Ser-Thr-Tyr-Pro-Ser-Cys—Cys-Cys-Ile-Lys-Pro-Ser-Asp-Gly-Asn-TyT-Thr-Tyr (SEQ ID NO:31).

The invention provides a vector comprising DNA which codes for a hepatitis B surface antigen protein of the invention, a fragment thereof, or a particle containing the protein.

The invention provides a method of detecting in a sample a nucleic acid sequence coding for a mutant hepatitis B surface antigen protein comprising: (a) providing a sample suspected of containing a nucleic acid sequence coding for a mutant hepatitis B surface antigen protein of the invention; and (b) detecting the nucleic acid sequence coding for the mutant hepatitis B surface antigen protein. In a preferred embodiment, prior to the detecting step (b) at least a portion of the nucleic acid sequence is amplified. In another embodiment, the detecting step is performed by hybridizing the amplified nucleic acid with at least a portion of a nucleotide probe comprising a nucleotide sequence complementary to the amplified mutant hepatitis B nucleic acid; and detecting the probe. In another embodiment the probe is labeled. In still another embodiment, the hybridized probe and amplified nucleic acid complex is detected by a specific binding agent which is specific to double-stranded DNA; the specific binding agent preferably is a monoclonal antibody or a fragmentary monoclonal antibody. In another embodiment, the detecting step is performed by separating the amplified nucleic acid according to nucleotide sequence length and detecting nucleotide sequences corresponding to amplified hepatitis B nucleic acid.

The invention provides a nucleotide probe which comprises a nucleotide sequence selected from:

sense probe #1 (from nt 491 to nt 526):

5'-GGA YTM TCG ACC ATC MGC ACG GGA GCA TAC CAA CCC-3' (SEQ ID NO:34);

antisense probe #2 (from nt 526 to nt 491):

5'-GGG TTG GTA TGC TCC CGT GCK GAT GGT CGA KAR TCC-3' (SEQ ID NO:35);

sense probe #3 (from nt 500 to nt 523):

25 5'-ACC ATC MGC ACG GGA GCA TAC CAA-3' (SEQ ID N0:36);

antisense probe #4 (from nt 523 to nt 500):

5'-TTG GTA TGC TCC CGT GCK GAT GGT-3'(SEQ ID NO:37);

sense probe #5 (from nt 488 to nt 511):

5'-CCA GGA YTM TCG ACC ATC MGC ACG-3'(SEQ ID NO:38);

antisense probe #6 (from nt 5 14 to nt 491):

5'-TCC CGT GCK GAT GGT CGA KAR TCC-3'(SEQ ID N0:39);

sense probe #7 (from nt 515 to nt 538):

5'-GCA TAC CAA CCC TGC ACG ACT ATT G-3'(SEQ ID NO:40);

antisense probe #8 (from nt 538 to nt 515):

5'-C AAT AGT CGT GCA GGG TTG GTA TGC-3'(SEQ ID NO:41);

sense probe #9 (from nt 573 to nt 605):

5'-GT ATC AAA CCT TCG GAC GGA AA,RTAC ACC TAT A-3'(SEQ ID NO:42);

sense probe #10 (from nt 584 to nt 605):

5'-TCG GAC GGA AAT TAC ACC TAT A-3'(SEQ ID NO:43);

antisense probe #11 (from nt 616 to nt 595):

5'-TGG GAT GGG AAT ATA GGT GTA A-3'(SEQ ID NO:44);

or a nucleotide sequence having substantially the same nucleotide sequence and having substantially the same hybridization activity of any of the listed nucleotide sequences. In a preferred embodiment, the probe consists essentially of one of the sequences listed above. In a preferred embodiment, these probes are used in the methods and kits of the invention. These probes may further comprise a detectable label. Primers appropriate for use with these probes are apparent to one of skill in the art.

The invention provides a kit for the detection of a nucleic acid sequence coding for a mutant hepatitis B surface antigen protein of the invention comprising: at least one reagent comprising nucleotide primer capable of annealing to and priming for amplification with nucleic acid characteristic for hepatitis B surface antigen; and at least one reagent comprising a nucleotide probe capable of hybridizing with the amplified mutant hepatitis B surface antigen nucleic acid.

Hepatitis B surface antigen DNA was cloned and sequenced from a serum sample taken from a kidney transplant patient (designated CTS) who tested positive for hepatitis B surface antigen (HBsAg) in an ETI-MAK-3 assay (Sorin Diagnostics, Saluggia, Italy) and negative in an AXSYM-HBsAg assay (Abbott Laboratories). The hepatitis B surface antigen designated CTS was not detected by the Abbott assay due to a mutation of the hepatitis B virus. Using an assay that provides false negative indications could result in a delay in providing effective treatment to a patient infected by the mutation or allow transmission of the mutant HBV from a blood donor to a recipient.

When the cloned nucleotide sequence is translated, its product displays a large number of mutations which are believed to determine differences in the secondary and tertiary structure of the antigen. Such mutations also determine differences in the antigenicity of the protein.

This mutant HBsAg-CTS is most closely homologous to native HBsAg of the ayw subtype. The relative homology suggests that the HBsAg-CTS evolved from the ayw subtype. Similarities notwithstanding, HBsAg-CTS possesses certain characteristics, which suggest that it is phylogenically removed from the ayw subtype in a significant way. In particular, the d/y determinant, identified by the presence of a basic amino acid (Arg (R) or Lys (K)) in position 122 is missing in HBsAg-CTS. Instead, the mutant HBsAg-CTS has a glutainine (Gln (Q)) residue in this position. Notably, however, the w/r determinant is maintained, as the residue in position 160 is a lysine (Lys (K)). The w/r determinant is identified by the presence of a basic amino acid (Arg (R) or Lys (K)) in position 160.

Other significant differences can be found as well. For example, in HBsAg-CTS, the residues at positions 121, 147, and 149, which are commonly cysteine (Cys (C)) have been replaced by tyrosine (Tyr (T)). Notably, positions 121, 147, and 149 are considered to be very important for the folding of the a determinant of HBsAg into a double loop, stabilized by disulfide bridges, in the relevant portion of the protein. Such stabilized double loops are a characteristic of the a determinant and are believed to influence the antigenicity of the antigen. More importantly, the stabilized double loop at the a determinant of HBsAg represents the immunodominant epitope against which a host can produce antibodies. Because they have an abnormal conformation of the immunodominant epitope, mutant strains of the Hepatitis B virus may be able to evade detection using conventional assay methods.

It should be noted, however, that even lacking the double loop immunodominant epitope, it is still possible to have antibodies which bind to the mutant HBsAg via a conformational epitope. Also, antibodies may bind the mutant HBsAg via s sequential epitope. Likewise, a monoclonal antibody having an affinity to mutant HBsAg may be used in the manufacture of assays capable of detecting and quantifying mutant strains of the Hepatitis B virus and in vaccines capable of raising an immune response against such mutant strains of the Hepatitis B virus.

The HBsAg-CTS includes additional mutations. By analyzing the alignment of the amino acid sequence of HBsAg-CTS with amino acid sequences belonging to different Hepatitis B virus subtypes, eight other mutations appear in positions which are generally well conserved among the various subtypes. These additional mutations (at positions 96, 113, 117, 120, 123, 127, 133, 140, 147, and 149) are shown in Table 1 in which the conserved amino acids are those commonly found at the particular position among the various subtypes, and the substituted amino acids are those that may be found at those positions in HBsAg-CTS.

TABLE 1

| Position | Conserved Amino Acid | Substituted Amino Acid |
|---|---|---|
| 96 | Val | Ala |
| 113 | Ser/Thr | Leu |
| 117 | Ser | Arg |
| 120 | Pro | Ala |
| 121 | Cys | Tyr |
| 122 | Lys | Gln |
| 123 | Thr | Pro |
| 127 | Pro | Ile |
| 133 | Met | Thr |
| 140 | Thr | Ile |
| 147 | Cys | Tyr |
| 149 | Cys | Tyr |

The DNA that codes for the mutant HBsAg-CTS comprises the following sequence of 276 nucleotides:

```
                                          (SEQ ID NO:1)
TGTCTGCGGCGTTTTATCATCTTCCTCTTCATCCTGCTGCTATGCCTCA
TCTTCTTGTTGGCTCTTCTGGACTATCAAGGTATGTTGCCCGTTTGTCC
TCTAATTCCAGGACTCTCGACCATCCGCACGGGAGCATACCAACCCTGC
ACGACTATTGCTCAAGGAACCTCTACGTATCCCTCCTGTTGCTGTATCA
AACCTTCGGACGGAAATTACACCTATATTCCCATCCCATCATCCTGGGC
TTTCGGAAAAYYCCTATGGGAGTGGGCCTCA
```

This sequence of 276 nucleotides encodes the following sequence of 92 amino acids:

```
Cys Leu Arg Arg Phe Ile Ile Phe Leu   (SEQ ID NO:2)
1               5

Phe Ile Leu Leu Leu Cys Leu Ile Phe
10                  15

Leu Leu Ala Leu Leu Asp Tyr Gln Gly
    20                  25

Met Leu Pro Val Cys Pro Leu Ile Pro
        30                  35

Gly Leu Ser Thr Ile Arg Thr Gly Ala
            40                  45

Tyr Gln Pro Cys Thr Thr Ile Ala Gln
                50

Gly Thr Ser Thr Tyr Pro Ser Cys Cys
55                  60

Cys Ile Lys Pro Ser Asp Gly Asn Tyr
    65                  70

Thr Tyr Ile Pro Ile Pro Ser Ser Trp
        75                  80

Ala Phe Gly Lys Phe Leu Trp Glu Trp
            85                  90

Ala Ser
```

In SEQ ID NO:2 the amino acid positions are numbered sequentially beginning with "1". To convert these positions to the standard positions in the HBsAg genome, add "75" to each position. This transformation is necessary for SEQ ID NOS:2–6. To convert the positions in SEQ ID NOS:7–27 to the standard positions in the HBsAg genome, add "33" to each position. In FIG. 1, SEQ ID NO:2 is presented using single letter symbols for the amino acids. Both the nucleotide sequence (SEQ ID NO:1) and the amino acid sequence (SEQ ID NO:2) are only portions of the entire sequences; the DNA coding for the major protein of HBsAg has a total of 226 amino acids.

Mutations of the HBsAg-CTS are readily apparent when the 92 amino acid sequence (SEQ ID NO:2) is aligned with different subtypes of HBsAg (ayw 3, adr, adw 2, and ayw). Partial sequences for these different subtypes are given in the attached sequence listing. (SEQ ID NO:3 is from HBVAYW3, SEQ ID NO:4 is from HBVADR, SEQ ID NO:5 is from HBVADW2, and SEQ ID NO:6 is from H4BVAYW.) For ease of comparison, the sequences are compared with SEQ ID NO:2 in FIG. 2, using the single letter symbols for amino acids. In these alignments, the mutant amino acids are represented in bold and underlined.

Expansion of the comparison to multiple species within each subtype has been carried out with amino acid sequences that are 154 amino acids in length. In these analyses, HBsAg-CTS is compared to twenty different HBsAg species contained within four different HBsAg subtypes. Partial sequences for these different subtypes are given in the attached sequence listing. SEQ ID NO:7 is from 7AYWS, SEQ ID NO:8 is from 6AYWS, SEQ ID NO:9 is from 3AYWS, SEQ ID NO:10 is from 2AYWS, SEQ ID NO:11 is from 1AYWS, SEQ ID NO:12 is from 1ADYAVS, SEQ ID NO:13 is from 5AYWS, SEQ ID NO:14 is from 5ADWS HBVAYW, SEQ ID NO:15 is from 2ADWS, SEQ ID NO:16 is from 3ADWMUT, SEQ ID NO:17 is from 2ADWMUT, SEQ ID NO:18 is from 1ADWS, SEQ ID NO:19 is from 4ADWMUT, SEQ ID NO:20 is from 3ADWS, SEQ ID NO:21 is from 1ADWMUT, SEQ ID NO:22 is from 4ADRS, SEQ ID NO:23 is from 1ADRS, SEQ ID NO:24 is from 3ADRS, SEQ ID NO:25 is from 2ADRS, SEQ ID NO:26 is from 4ADWS, and SEQ ID NO:27 is from CTS.

For ease of comparison the sequences are compared with SEQ ID NO:2 in FIG. 3, using the single letter symbols for amino acids. In these alignments, the mutant amino acids are represented in bold and underlined. The symbol "*" indicates that a position in the alignment is perfectly conserved in the mutant, and the symbol "." indicates that a position in the alignment is well conserved in the mutant.

In these 154 amino acid sequences, the mutant HB sAg-CTS had 100 amino acids (64.9%) that were identical ("perfectly conserved") to the amino acids in the corresponding position of each of the other twenty subtypes, and 32 amino acids (20.8%) that were similar ("well conserved") to the amino acids in the corresponding position of the other twenty subtypes.

Amino acid homology between the inventive isolate and the other subtypes is presented in Table 2. Nucleoltide and deduced amino acid sequences were analyzed employing the CLUSTAL program contained in the PC/GENE software package (IntelliGenetics, Mountain View, Calif.); the sequences used in the alignments were downloaded from the GenBank Database (accession numbers: J02203, X59795, X65257, X77310, X77308, X65258, J02202, D00329, D00330, X51970, X69798, M54923, S81945, S81946, D16665, X01587, S50225, D23677, D23678, and Z72478).

TABLE 2

| | ayw | adw/1 | adw/2 | adr |
|---|---|---|---|---|
| CTS | 89–91% | 82–83% | | 83–94% |
| ayw | >96% | 89–91.5% | | 88–92% |
| adw/1 | — | 98% | 92–93% | — |
| adw/2 | — | — | 96% | — |
| adr | — | 89–92% | | >96% |

Figure 5:
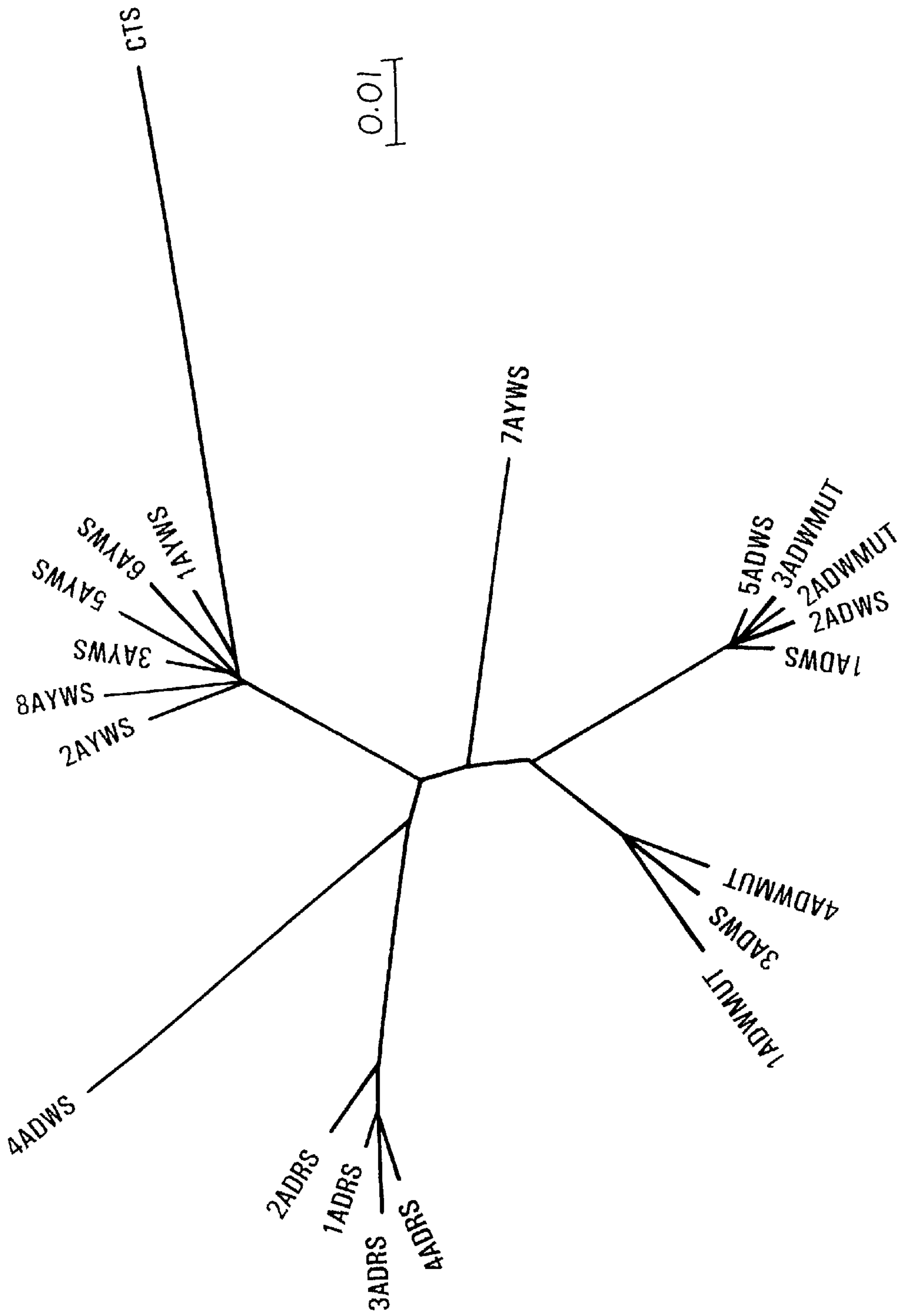

A phylogenic analysis, comparing the 154 amino acid sequence from HBsAg-CTS (SEQ ID NO:27) to equally-sized fragments of the twenty species (SEQ ID NOS:7–26) was performed using the PHYLIP package (Phylogenetic Inference Package) version 3.5c 1993, directly distributed from Dr. J. Felsenstein, Department of Genetics, University of Washington, Seattle. The clustering of the different subtypes was achieved by performing a bootstrap analysis using the SEQBOOT program, also contained in the PHYLIP package, resampling the data 250 times, in order to eliminate some factors which can have an a specific influence on the various phylogenic clusters. The results of the phylogenic analysis are presented in FIGS. 4 and 5. In FIG. 4, which seeks to identify relevant subtypes, it is seen that the HBsAg-CTS mutant is a member of the ayw subtype of HBsAg. In FIG. 5, however, the phylogenic distance of HBsAg-CTS from the ayw subtype of HBsAg is clearly evident. In FIG. 5, the length of the branch is proportional to the phylogenic length.

Phylogenic distances of the HBsAg-CTS from the different HBsAg subtypes, and of the different HBsAg subtypes from one another, are presented in Table 3.

TABLE 3

| | ayw | adw/1 | adw/2 | adr |
|---|---|---|---|---|
| CTS | 0.097–0.119 | 0.191–0.200 | | 0.175–0.191 |
| ayw | <0.04 | 0.089–0.119 | | 0.082–0.127 |
| adw/1 | — | <0.0131 | 0.068–0.082 | — |
| adw/2 | — | — | <0.033 | — |
| adr | — | 0.082–0.119 | | <0.033 |

The data of Tables 2 and 3 and FIGS. 4 and 5 suggest that HBsAg-CTS evolved from the ayw subtype; however, its phylogenic distance from the ayw subtype is comparable to distances seen between the various subtypes. Additionally, the phylogenic distance of the HBsAg-CTS from the other members within the ayw subtype is much greater (0.097–0.119) than the phylogenic distances existing within each of the various subtypes (<0.04).

HBsAg-CTS has been confirmed as an escape mutant by means of a neutralization assay following the protocol described in the REAC 801 Confirmatory Test (FDA License No. 89-0376). Three neutralizing solutions were used: (a) human plasma anti-HBsAg positive (used in a kit identified as REAC 801, natural infection, available from Sorin Diagnostics, Saluggia, Italy), (b) human IgG anti-HBsAg positive (Biagini serum, a natural infection material used in passive prophylaxis, available from Farma Biagini S.p.A.), and (c) human serum obtained from a donor after vaccination with ENGERIX-B vaccine, available from SmithKline Beecham.

A protocol, approved by the U.S. Food and Drug Administration, was used in which a sample was considered neutralized, and thereby confirmed HBsAg positive, when greater than 30% neutralization occurred. Of course, it should be noted that 30% is a relative value which can be influenced by the potency of the neutralizing antibody and the concentration of antigen in the sample. Relative comparisons between the different antigens and antibodies was achieved by normalizing the neutralizing antibodies at different concentrations. These concentrations were expressed in mIU. Although it is more difficult to normalize the concentration of the antigen, it was quantified to a concentration of approximately 1.3 PEI U/mL (PEI is an abbreviation for the Paul Erlich Institut, Germany) for the natural HBsAg subtype ad, and to approximately 0.5 PEI U/mL for the mutant (CTS) Under these conditions, it is expected that the antibodies will inhibit the mutant to a much higher degree than the natural species. This is true because of the concentration: there is a higher ratio of antibodies to antigen for the mutant antigen in comparison with the natural one. So because the neutralization of the mutant antigen is lower than the neutralization of the natural antigen, these results show very clearly that the mutant should be introduced both in vaccines and diagnostic reagents.

The results of the neutralization assay, are presented below. In each of the assays, the HBsAg detection was performed using an ETI-MAK-2 PLUS kit, lot PP885 (available from Sorin Diagnostics, Saluggia, Italy); this kit contains REAC 801 Sol. A. Results are shown in Table 4:

TABLE 4

| Specimen | REAC 801 Sol. A O.D. |
|---|---|
| Negative Control (NC) | 0.027 |
| Positive Control (PC) (1 UPEI/mL) | 1.490 |
| Cut off | 0.077 |
| CTS (0.5 UPEI/mL) | 0.804 |
| natural HBsAg subtype ad (1.3 UPEI/mL) | 1.799 |

The results reported in Table 4 show the values obtained on the tested specimen by using an HBsAg negative human serum in the neutralization assay (Sol. A of REAC 801) in order to determine the baseline of the HBsAg positive specimen in non-inhibited form, to compute the percent of neutralization.

The results of the neutralization assays for the three sample solutions are shown in Tables 5 to 7.

TABLE 5

| | REAC 801 (Human Plasma anti-HBs+) | | | | | |
|---|---|---|---|---|---|---|
| Samples | 10000 mIU/mL (anti-HBs) | % neu | 1000 mIU/mL (anti-HBs) | % neu | 100 mIU/mL (anti-HBs) | % neu |
| CP | 0.418 | 73 | 1.029 | 32 | 1.372 | 8 |
| CTS | 0.385 | 54 | 0.782 | 3 | 0.825 | −3 |
| HBsAg | 0.366 | 81 | 1.236 | 32 | 1.759 | 2 |

TABLE 6

| | hIgG anti-HBs (Biagini Serum) | | | | | |
|---|---|---|---|---|---|---|
| Samples | 10000 mIU/mL (anti-HBs) | % neu | 1000 mIU/mL (anti-HBs) | % neu | 100 mIU/mL (anti-HBs) | % neu |
| CP | 0.416 | 73 | 0.855 | 43 | 1.135 | 24 |
| CTS | 0.356 | 58 | 0.610 | 25 | 0.677 | 16 |
| HBsAg | 0.354 | 82 | 0.931 | 49 | 1.329 | 27 |

TABLE 7

| Vaccinated Serum (ENGERIX-B) | | | | | | |
|---|---|---|---|---|---|---|
| Samples | 10000 mIU/mL (anti-HBs) | % neu | 1000 mIU/mL (anti-HBs) | % neu | 100 mIU/mL (anti-HBs) | % neu |
| CP | 0.451 | 71 | 0.884 | 41 | 1.273 | 15 |
| CTS | 0.416 | 50 | 0.745 | 8 | 1.090 | −37 |
| HBsAg | 0.251 | 87 | 1.048 | 42 | 1.594 | 12 |

Finally, the ratios of antibody potency (Ab, expressed in mIU/mL) to antigen concentration (Ag, expressed in PEI U/mL) are shown in Tables 8 to 10 below.

TABLE 8

| REAC 801 (Human Plasma anti-HBs+) | | | |
|---|---|---|---|
| CTS Ab/Ag | % neutralization | natural HBsAg Ab/Ag | % neutralization |
| 20 | 54 | 7.7 | 81 |
| 2 | 3 | 0.8 | 32 |
| 0.2 | −3 | 0.1 | 2 |

TABLE 9

| hIgG anti-HBs (Biagini Serum) | | | |
|---|---|---|---|
| CTS Ab/Ag | % neutralization | natural HBsAg Ab/Ag | % neutralization |
| 20 | 58 | 7.7 | 82 |
| 2 | 25 | 0.8 | 49 |
| 0.2 | 16 | 0.1 | 27 |

TABLE 10

| Vaccinated Serum (ENGERIX-B) | | | |
|---|---|---|---|
| CTS Ab/Ag | % neutralization | natural HBsAg Ab/Ag | % neutralization |
| 20 | 50 | 7.7 | 87 |
| 2 | 8 | 0.8 | 42 |
| 0.2 | −37 | 0.1 | 12 |

Figure 6:
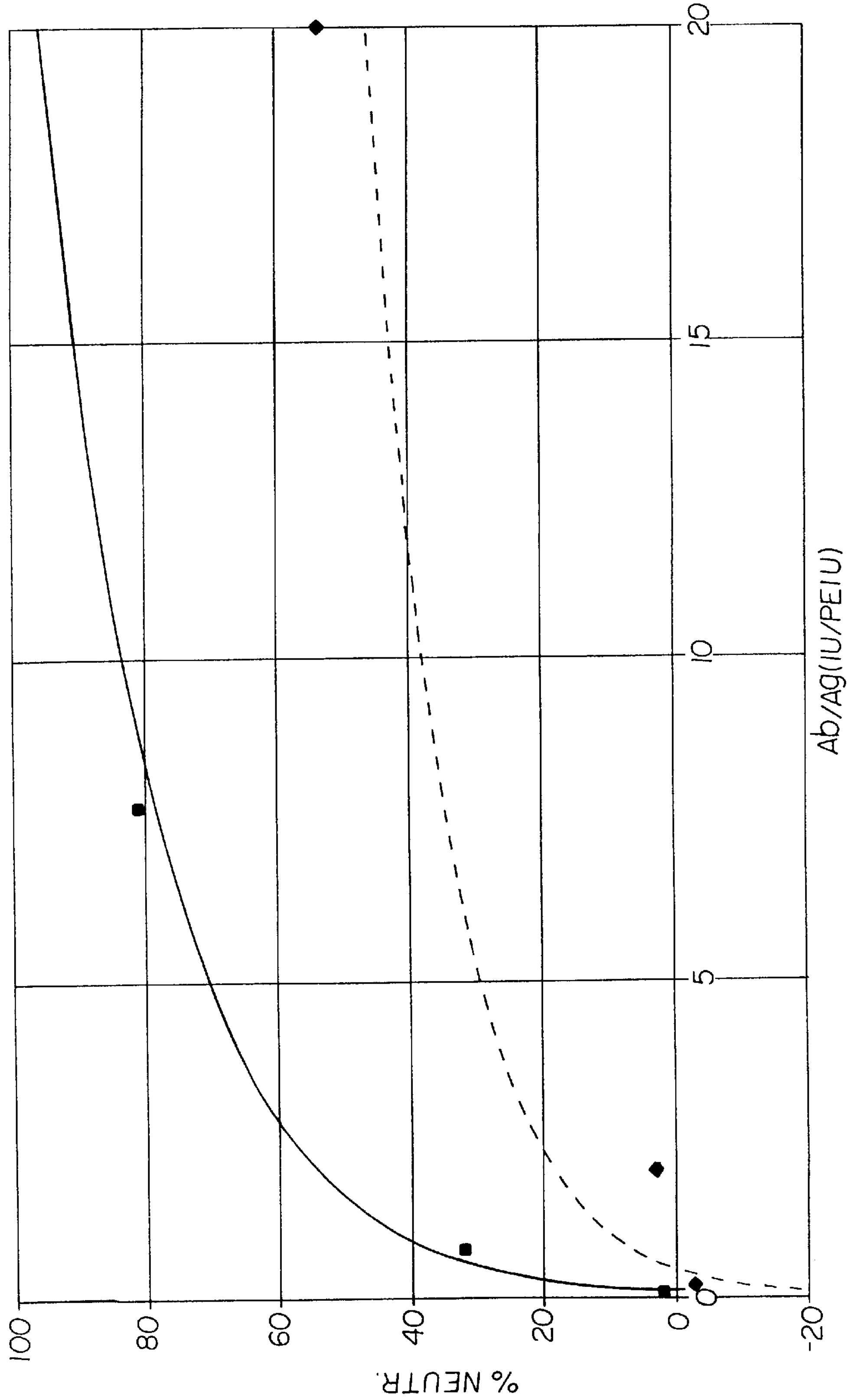
FIG. 6 is a graphical representation of the data of Table 8, plotting percent neutralization as a function of the ratio of antibody potency to antigen concentration.
Figure 7:
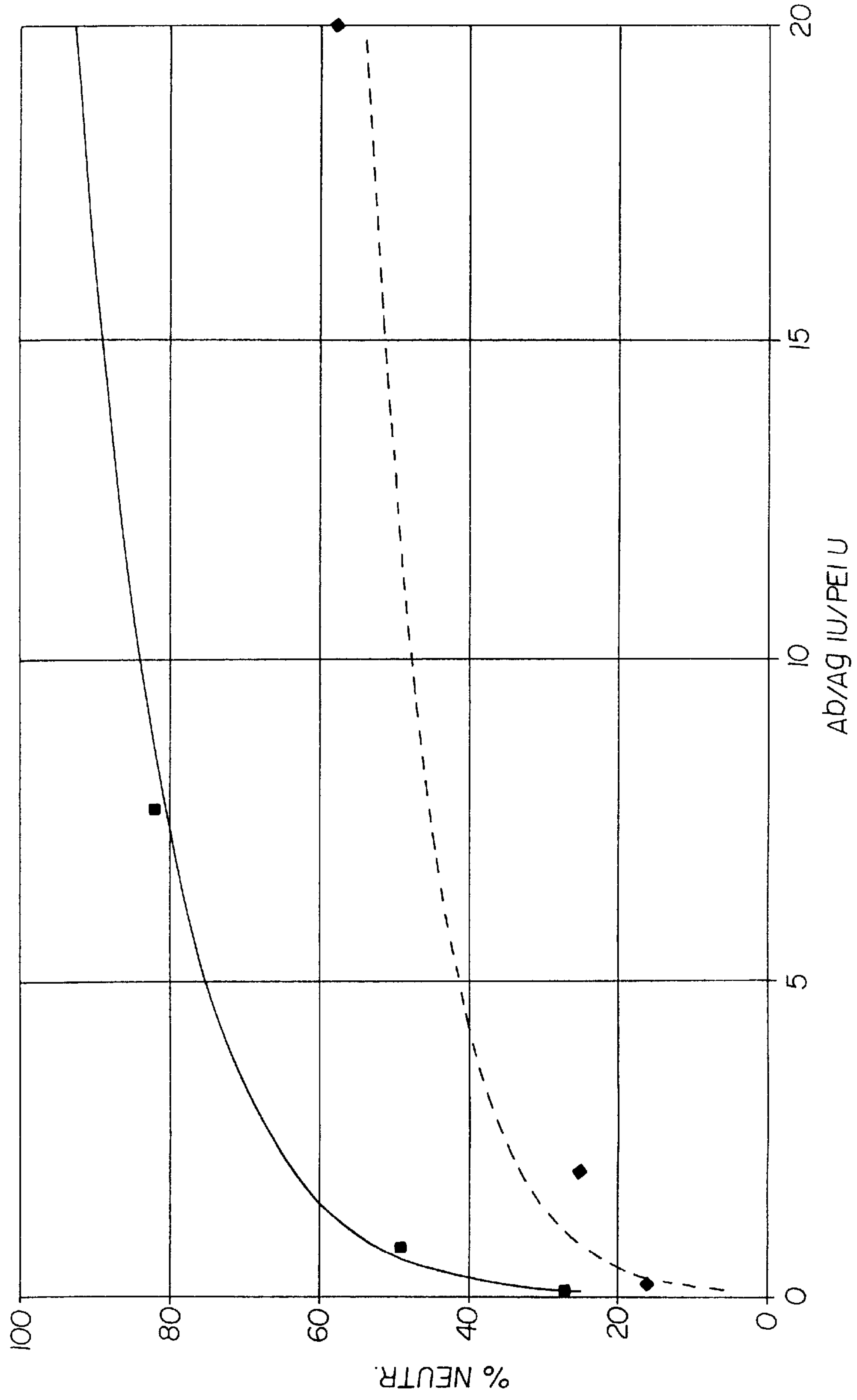
FIG. 7 is a graphical representation of the data of Table 9, plotting percent neutralization as a function of the ratio of antibody potency to antigen concentration.
Figure 8:
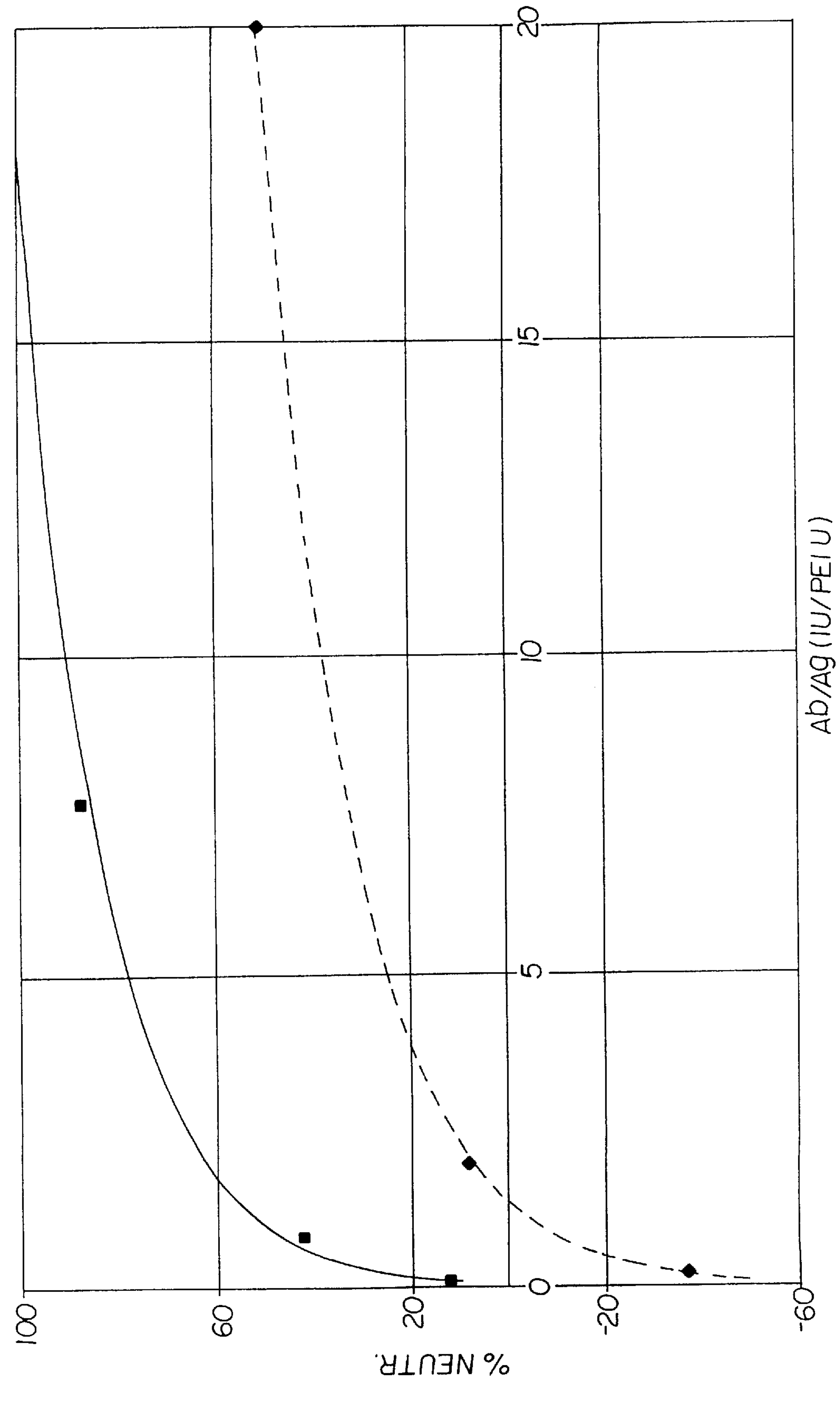
FIG. 8 is a graphical representation of the data of Table 10, plotting percent neutralization as a function of the ratio of antibody potency to antigen concentration.

The results of Tables 8 to 10 are also shown graphically, plotted in FIGS. 6 to 8, respectively. The data shown in Tables 8 to 10 and FIGS. 6 to 8 demonstrate that HBsAg-CTS is an escape mutant.

As noted above, the presence of HBsAg-CTS was detected in an ETI-MAK-3 assay, but not detected in an AXSYM-HBsAg assay. This result suggests that the AXSYM-HBsAg assay depends upon the presence of the immunodominant epitope “a” which has a mutated conformation in HBsAg-CTS. In contrast, the ETI-MAK-3 assay detects the immunodominant epitope “a” in the natural or mutated conformation. It is noted that as used herein, the terms “detect” and “detection” and “determination” in the context of an immunoassay are intended to mean either one or both of determining the presence or the amount of a target species in a sample.

The ETI-MAK-3 assay provides for the qualitative determination of HBsAg using a direct, non-competitive sandwich assay which employs enzyme linked immunosorbent assay (ELISA) technology. In general terms, a monoclonal antibody having an affinity for HBsAg is bound to a surface, such as the wall of a microtiter well. The antibody is exposed to a sample which may or may not contain HBsAg. If HBsAg is present in the sample, it will become bound to the antibody forming antibody/HBsAg complexes. The surface is then exposed to an enzyme tracer which will bind to the antibody/HBsAg complexes. By detecting the level of bound tracer, it is then possible to determine the level of HBsAg in the sample. One preferred tracer is an anti-HBsAg antibody obtained from sheep to which is bound a horseradish peroxidase.

Commercially available assays typically include a variety of reagents necessary to determine the presence of a particular biological material. For example, the ETI-MAK-3 assay includes a microtiter plate having wells coated with a monoclonal antibody having an affinity for HBsAg, an enzyme tracer, positive and negative control solutions, tracer diluent, wash buffer, chromogen solution, substrate solution, and a blocking reagent. These last three reagents are used to properly develop a detectable signal indicative of the presence and level of tracer (and thereby antigen) in the sample.

The present invention is particularly useful for the manufacture of immunoassay kits for the Hepatitis B virus in that it may be used to ensure that the monoclonal antibody provided in such kits maintains its affinity to HBsAg even in the absence of the immunodominant epitope in its natural conformation. Specifically, mutant Hepatitis B virus may not be detected in assays which rely upon detection of the immunodominant epitope (a) of HBsAg in its natural conformation. Thus, detection of the mutant strain requires the use of an antibody that binds to the mutant antigen. In order to assure that the antibodies used in the immunoassay kits will detect the mutant Hepatitis B virus, the assay manufacturing process requires that the supplied antibodies maintain their affinity for the mutant antigen. This may be achieved in manufacture by exposing antibody specimens to a known calibration standard of the mutant antigen and then detecting the presence and level of the antigen. If the assay provides an accurate determination, then the antibody will be provided in the immunoassay kit. If the assay fails to provide an accurate determination, then the antibody should be replaced with one that meets the immunoassay requirements. In so doing, it is assured that the commercial immunoassay kits will have the ability to detect the presence and level of HBsAg in a sample, even if the HBsAg is of the mutant variety lacking the immunodominant epitope.

Mutant HBsAg may also be provided in the positive control reagent supplied with the immunoassay kit. Such positive controls typically contain HBsAg that has been heat-inactivated and preserved. For example, the positive control of the ETI-MAK-3 assay is a 2.5 mL sample of human recalcified plasma having a maximum concentration of heat-inactivated and preserved HBsAg (subtypes ad and ay) of 0.4–1 U/mL.

Of course, it should be apparent that the present invention is not intended to be limited to a specific type of diagnostic assay or kit, but rather is intended to include any of a wide variety of diagnostic assays and kits for conducting such assays. Assays can include but are not limited to those based on competition, direct reaction, or sandwich-type assays. Assays may use solid phases or may be performed by immunoprecipitation or any other methods which do not utilize solid phases.

Assays can take many formats. Some depend upon the use of labeled specific binding molecules such as antibodies, whereas some detect the interaction of antibody (or other specific binding agent) and antigen by observing the resulting precipitation. Examples of qualitative and quantitative assays which do not rely on labeled antibodies include gel precipitation, single radial immunodiffusion, immunoelectrophoresis, including rocket electrophoresis and two-dimensional electrophoresis, and quantification by the scattering of an incident light source (nephelometry). A preferred assay is an agglutination assay; examples of agglutination assays are provided in U.S. Pat. Nos. 5,286,452 (Hansen) and U.S. Pat. No. 5,589,401 (Hansen et al.).

Often, some form of labeling is used to detect the antigen-antibody interaction. Labels may be radioactive or non-radioactive. Depending on the format of the assay, either the specific binding agents of the invention can be labeled, or other specific binding agents which bind to them may be labeled. Immunoassays (including radioimmunoassays) and immunometric assays (including immunometric radioassays and enzyme-linked immunosorbent assays) can be used, as can immunoblotting techniques. Chemiluminescent, fluorescent, enzyme, biohliminescent, and epifluorescent labels are also contemplated. IMX assays of the type sold by Abbott Laboratories, Chicago, Ill., U.S.A., are also contemplated.

Assays for mutant hepatitis B nucleic acid may also be used. In these methods a nucleic acid probe is used to detect a nucleic acid sequence that codes for the mutant hepatitis B surface antigen protein. Amplification methods such as the polymerase chain reaction may be used in conjunction with the nucleic acid probe. A preferred method of assaying for mutant hepatitis B nucleic acid uses a method known as an DNA enzyme immunoassay (DEIA) in which a probe hydridizes with single-stranded DNA and the hybridized probe-DNA complex is detected with a monoclonal antibody that can discriminate between single-stranded and double-stranded DNA. DEIA assays are described in Mantero et al., *Clin. Chem.*, 37/3:422–429 (1991).

In addition to its use in diagnostic assays, the escape mutant HBsAg of the present invention may also be used in a vaccine to the Hepatitis B virus. In particular, the vaccine can contain an immunogenic amount of the inventive escape mutant in a pharmaceutically acceptable carrier. Immunogenic amounts of the vaccine can be determined using methods well-known to those having ordinary skill in the art. The pharmaceutically acceptable carrier can comprise saline or other suitable carriers, and may also include various additives, adjuvants, and the like. In addition, the vaccine may contain other HBV antigens such as normal HBsAg or composite HBsAg particles containing all or part of the pre-S1 or pre-S2 polypeptides.

AMPLIFICATION PROTOCOL

The "S" gene of HBV has a total length of 657 nucleotides (from nt 157 to nt 837, numbering from the unique EcoR I site of HBV genome); this gene encodes for a protein of 219 amino acids named HBsAg. Two primers were used to perform the amplification reaction and these primers have targets within this range from nt 157 to nt 837.

The amplification of 45 cycles was performed using the following primers:

primer sense "a4"5'-CTC GTG GTG GAC TTC TCT CAA TTT-3' (SEQ ID NO:32) (nucleotides 255–278);

primer antisense "a5"5'-GGA AAG CCC TAC GAA CCAO CTG-3' SEQ ID NO:33)(nucleotides 717–697).

The "S" gene fragment amplified had a total length of 463 nt, coding for a polypeptide of 154 aa (including the amino acid residues 34 and 187 of the HBsAg).

The composition of the reaction mix was Tris HCl pH=8.8 (67 mM), $(NH_4)_2SO_4$ (1.6 mM), $MgCl_2$ (2 mM), 2-mercaptoethanol (10 mM), 100 ug/mL of bovine serum albumin, deoxyribonucleotide triphosphates (dNTPs) (200 uM each), 2.5 U of Taq DNA Polymerase (Perkin Elmer), and 50 pmoles of each primer.

Before amplification, an aliquote of the serum sample was boiled for 5 minutes and then centrifuged at 14000 rpm (4° C.) for 15 minutes; the supernatant was recovered and the amplification was carried out in a total volume of 50 $\mu$L using 5 $\mu$L of the treated sample.

Each cycle of the amplification, for a total of 45 cycles, included a denaturation step at 94° C. for 1 minute, an annealing step at 64° C. for 1 minute and an extension step at 72° C. for 1 minute; the last cycle had an extension time of 10 minutes to improve the cloning efficiency and the amplification was carried out with a Perkin Elmer Thermal Cycler.

The amplification product of 463 bp, after purification on agarose gel with Qiaex resin (Qiagen GmbH, Hilden, Germany), was cloned into the pCR2.1 vector (Invitrogen, San Diego, Calif.), transformed in XL-1 blue *E. coli* strain and a subsequent screening was performed on the colonies to identify the positive clones.

Four clones were chosen to be sequenced, and all of them gave identical results.

In more detail, the clones was grown overnight at 37° C. in LB-broth supplemented with ampicillin; the next day the plasmid DNA was purified from 5 ml of the liquid culture using the Q1Awell system (Qiagen GmbH, Hilden, Germany).

The DNA template prepared in this way, that should be free from protein, chromosomal DNA, and organic solvents, was sequenced using the A.L.F. automated DNA sequencer and the Autoread Sequencing Kit (Pharmacia Biotech, Uppsala, Sweden).

This system employs a non-radiochemical approach to sequencing, in which a primer labeled with fluorescein at its 5'-terminus is annealed to the template.

Using standard dideoxy sequencing methods, the fluorescent primer was extended by T7 DNA Polymerase in four separate reactions, and then loaded on polyacrylamide gel.

The above description and accompanying drawings are provided for the purpose of describing embodiments of the invention and are not intended to limit the scope of the invention in any way. It will be apparent to those skilled in the art that various modifications and variations can be made in the isolated mutant hepatitis B surface antigen proteins, fragments thereof, and particles containing these proteins, specific binding agents thereto, and immunoassays and vaccines using these proteins, fragments thereof, and particles containing these proteins and/or specific binding agents without departing from the spirit or scope of the invention. Thus, it is intended that the present invention cover the modifications and variations of this invention provided they come within the scope of the appended claims and their equivalents.

What is claimed is:

1. An isolated mutant hepatitis B surface antigen protein which comprises an amino acid sequence of a surface antigen protein of hepatitis B virus which infects humans, in which the amino acid at position 121 is not cysteine and at least one of the amino acids, at positions 120, 122, 123, 147, or 149 is not a conserved amino acid for its position.

2. An isolated mutant hepatitis B surface antigen protein of claim 1, wherein at least one of the amino acids at positions 120, 122, or 123 is not a conserved amino acid for its position.

3. An isolated mutant hepatitis B surface antigen protein of claim 1, wherein at least one of the amino acids at positions 147 or 149 is not a conserved amino acid for its position.

4. An isolated mutant hepatitis B surface antigen protein of claim 1, wherein at least two of the amino acids at positions 120, 122, 123, 147, or 149 are not conserved amino acids for their positions.

5. An isolated mutant hepatitis B surface antigen protein of claim 1, wherein at least three of the amino acids at positions 120, 122, 123, 147, or 149 are not conserved amino acids for their positions.

6. An isolated mutant hepatitis B surface antigen protein of claim 1, wherein at least four of the amino acids at positions 120, 122, 123, 147, or 149 are not conserved amino acids for their positions.

7. An isolated mutant hepatitis B surface antigen protein of claim 1, wherein all five amino acids at positions 120, 122, 123, 147, or 149 are not conserved amino acids for their positions.

8. An isolated mutant hepatitis B surface antigen protein of claim 1, wherein the conserved cysteine at position 121 is replaced by tyrosine.

9. An isolated mutant hepatitis B surface antigen protein of claim 1, wherein the conserved proline at position 120 is replaced by alanine.

10. An isolated mutant hepatitis B surface antigen protein of claim 1, wherein the conserved lysine or arginine at position 122 is, replaced by glutamine.

11. An isolated mutant hepatitis B surface antigen protein of claim 1, wherein the conserved threonine at position 123 is replaced by proline.

12. An isolated mutant hepatitis B surface antigen protein of claim 1, wherein the conserved proline at position 120 is replaced by alanine, the conserved lysine or arginine at position 122 is replaced by glutamine, and the conserved threonine at position 123 is replaced by proline.

13. An isolated mutant hepatitis B surface antigen protein of claim 1, wherein the amino acid at position 127 is not a conserved amino acid for its position.

14. An isolated mutant hepatitis B surface antigen protein of claim 13, wherein the conserved proline at position 127 is replaced by isoleucine.

15. An isolated mutant hepatitis B surface antigen protein of claim 1, wherein the amino acid at position 117 is not a conserved amino acid for its position.

16. An isolated mutant hepatitis B surface antigen protein of claim 15, wherein the conserved serine at position 117 is replaced by arginine.

17. An isolated mutant hepatitis B surface antigen protein of claim 1, wherein the amino acid at position 96 is not a conserved amino acid for its position.

18. An isolated mutant hepatitis B surface antigen protein of claim 17, wherein the conserved valine at position 96 is replaced by alanine.

19. An isolated mutant hepatitis B surface antigen protein of claim 1, wherein the amino acid at position 113 is not a conserved amino acid for its position.

20. An isolated mutant hepatitis B surface antigen protein of claim 19, wherein the conserved serine or threonine at position 113 is replaced by leucine.

21. An isolated mutant hepatitis B surface antigen protein of claim 1, wherein the amino acid at position 133 is not a conserved amino acid for its position.

22. An isolated mutant hepatitis B surface antigen protein of claim 21, wherein the conserved methionine at position 133 is replaced by threonine.

23. An isolated mutant hepatitis B surface antigen protein of claim 1, wherein the amino acid at position 140 is not a conserved amino acid for its position.

24. An isolated mutant hepatitis B surface antigen protein of claim 23, wherein the conserved threonine, at position 140 is replaced by isoleucine.

25. An isolated mutant hepatitis B surface antigen protein of claim 1, wherein the amino acid at position 147 is not a conserved amino acid for its position.

26. An isolated mutant hepatitis B surface antigen protein of claim 25, wherein the conserved cysteine at position 147 is replaced by tyrosine.

27. An isolated mutant hepatitis B surface antigen protein of claim 1, wherein the amino acid at position 149 is not a conserved amino acid for its position.

28. An isolated mutant hepatitis B surface antigen protein of claim 1, wherein the conserved cysteine at position 149 is replaced by tyrosine.

29. An isolated mutant hepatitis B surface antigen protein of claim 1, wherein the amino acids at positions 147 and 149 are not conserved amino acids for their positions.

30. An isolated mutant hepatitis B surface antigen protein of claim 29, wherein the conserved cysteines at position 121, 147, and 149 are replaced by tyrosines.

31. An isolated mutant hepatitis B surface antigen protein of claim 1, wherein the amino acid at position 145 is the conserved glycine.

32. An isolated mutant hepatitis B surface antigen protein of claim 1, wherein the amino acids at positions 137, 138, and 139 are all conserved cysteines.

33. An isolated mutant hepatitis B surface antigen protein of claim 1, wherein the amino acid at position 124 is the conserved cysteine.

34. An isolated fragment of a mutant hepatitis B surface antigen protein of claim 1 in which the isolated fragment comprises a sequence of at least thirty amino acids, said sequence comprising the amino acids at positions 120 to 149, in which the amino acid at position 121 is not cysteine and at least one of the amino acids, at positions 120, 122, 123, 147, or 149 is not a conserved amino acid for its position.

* * * * *